US008541603B2

(12) United States Patent
Old et al.

(10) Patent No.: US 8,541,603 B2

(45) **Date of Patent: *Sep. 24, 2013**

(54) SUBSTITUTED CYCLOPENTANES OR CYCLOPENTANONES AS THERAPEUTIC AGENTS

(75) Inventors: David W. Old, Irvine, CA (US); Todd S. Gac, Santa Ana, CA (US); Vinh X. Ngo, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/992,229

(22) PCT Filed: May 13, 2009

(86) PCT No.: PCT/US2009/043703

§ 371 (c)(1), (2), (4) Date: Mar. 25, 2011

(87) PCT Pub. No.: WO2009/146255

PCT Pub. Date: Dec. 3, 2009

(65) Prior Publication Data

US 2011/0190301 A1 Aug. 4, 2011

Related U.S. Application Data

(60) Provisional application No. 61/056,403, filed on May 27, 2008.

(51) Int. Cl.

| | |
|---|---|
| ***A61K 31/381*** | (2006.01) |
| ***C07C 59/62*** | (2006.01) |
| ***C07D 333/38*** | (2006.01) |

(52) U.S. Cl.

USPC ............... 549/64; 549/429; 560/51; 562/405; 564/170

(58) Field of Classification Search

USPC ..................... 549/64, 429; 560/51; 562/405; 564/170

See application file for complete search history.

(56) References Cited

U.S. PATENT DOCUMENTS

| | | | | |
|---|---|---|---|---|
| 4,166,452 | A | 9/1979 | Generales, Jr. | |
| 4,256,108 | A | 3/1981 | Theeuwes | |
| 4,265,874 | A | 5/1981 | Bonsen | |
| 5,462,968 | A | 10/1995 | Woodward | |
| 5,698,598 | A | 12/1997 | Woodward | |
| 6,090,847 | A | 7/2000 | Woodward | |
| 6,437,146 | B1 | 8/2002 | Hattori | |
| 6,476,064 | B1 | 11/2002 | Old et al. | |
| 6,710,072 | B2 | 3/2004 | Burk et al. | |
| 7,091,231 | B2 | 8/2006 | Donde | |
| 7,429,669 | B2 * | 9/2008 | Old et al. | 549/64 |
| 2007/0265464 | A1 | 11/2007 | Old et al. | |
| 2007/0293561 | A1 * | 12/2007 | Old et al. | 514/438 |
| 2011/0172299 | A1 * | 7/2011 | Gac et al. | 514/448 |

FOREIGN PATENT DOCUMENTS

| | | |
|---|---|---|
| WO | WO 93/14743 | 8/1993 |
| WO | WO 2008/008700 | 1/2008 |
| WO | WO 2008/064039 | 5/2008 |

OTHER PUBLICATIONS

Patani et al., Chem. REv. , 1996, 98(8), 3147-3176.*

U.S. Appl. No. 60/757,696, filed Jan. 10, 2006, David W. Old.

U.S. Appl. No. 60/947,904, filed Jul. 3, 2007, David W. Old.

U.S. Appl. No. 11/764,929, filed Jun. 19, 2007, David W. Old.

U.S. Appl. No. 60/805,285, filed May 4, 2006, David W. Old.

U.S. Appl. No. 60/746,391, filed May 4, 2006, Yariv Donde.

U.S. Appl. No. 60/746,386, filed May 4, 2006, Yariv Donde.

U.S. Appl. No. 60/746,835, filed May 22, 2006, Yariv Donde.

Remington's Pharmaceutical Sciences, Mack Publishing Company, Easton, Pa., 16th Edition, 1980.

Francis A. Carey, Organic Chemistry, New York: McGraw-Hill Book Company 1987, p. 63.

Collect. Czech. Chem. Commun. 1994, 58, 138-148.

Collect. Czech. Chem. Commun. 1994, 59, 2533-2544.

Buchwald, et al. (e.g. J. Org. Chem. 2006, 71, 430-433 and Tetrahedron Lett. 1997, 38, 6367-6370).

Buchwald (e.g. Tetrahedron 2004, 60, 7397-7403) and Hartwig (e.g. J. Am. Chem. Soc. 2006, 128, 2180-2181).

Peach, in Patai, "The Chemistry of the Thiol Group," pt. 2, pp. 735-744, Wiley, New York, 1974).

B. Resul et. al. : "Structure-Activity, Relationships of Prostaglandin Analogues as Ocular Hypotensive Agents. "Current Opinion in Therapeutic Patents,vol. 3, No. 6, 1993, pp. 781-795,p. 785.

* cited by examiner

*Primary Examiner* — Susannah Chung

(74) *Attorney, Agent, or Firm* — Lorenz Siddiqi; Allergan, Inc.

(57) ABSTRACT

Therapeutic compounds, methods, and compositions are disclosed herein for treating glaucoma and baldness in mammals. The specific compounds are described herein and are modified prostaglandin derivates.

21 Claims, No Drawings

SUBSTITUTED CYCLOPENTANES OR CYCLOPENTANONES AS THERAPEUTIC AGENTS

CROSS REFERENCE

This is a national stage application under 35 U.S.C. §371 of PCT patent application PCT/US09/43703, filed on May 27, 2009, which claims the benefit of U.S. Provisional Patent 61/056,403, filed on May 27, 2008, each of which is hereby incorporated by reference in its entirety.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

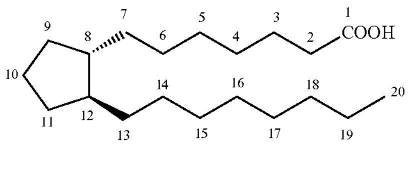

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

The prostaglandin E analog shown below is disclosed in the following documents, expressly incorporated herein by reference: U.S. Pat. No. 5,462,968; U.S. Pat. No. 5,698,598; and U.S. Pat. No. 6,090,847.

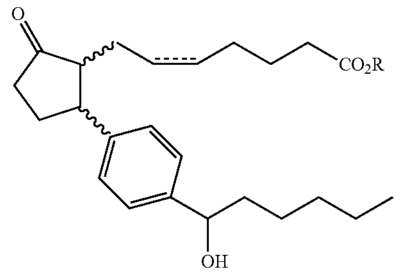

Other $EP_2$ selective agonists are disclosed in U.S. patent application Ser. No. 11/009,298, filed Dec. 10, 2004 (now U.S. Pat. No. 7,091,231 issued Aug. 15, 2006). Prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No. 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

SUMMARY OF THE INVENTION

Disclosed herein are compounds useful in treating glaucoma, inflammatory bowel disease, the stimulation of hair growth, and the stimulation of the conversion of vellus hair to terminal hair. The compounds themselves are disclosed below.

DESCRIPTION OF THE INVENTION

One embodiment is a compound according to the formula

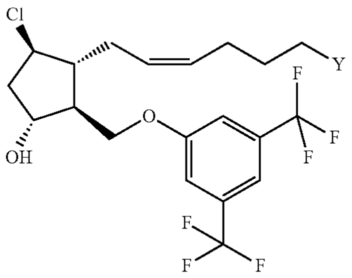

or a pharmaceutically acceptable salt or a prodrug thereof wherein Y is

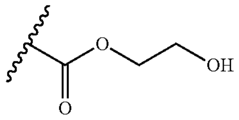

or

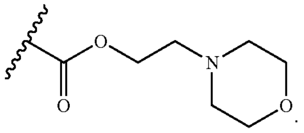

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

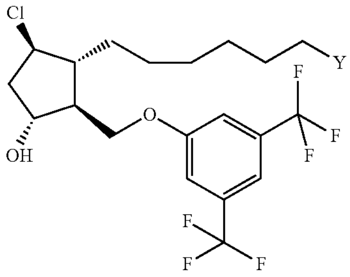

or a pharmaceutically acceptable salt or a prodrug thereof, wherein Y is

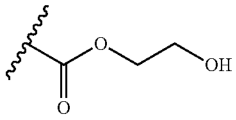

or

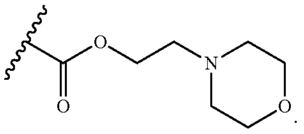

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

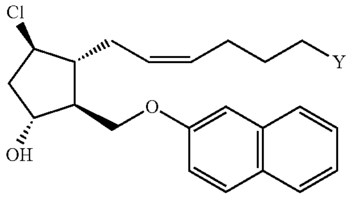

or a pharmaceutically acceptable salt or a prodrug thereof, wherein Y is

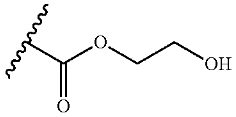

or

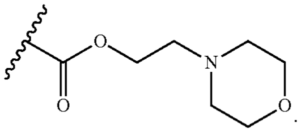

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

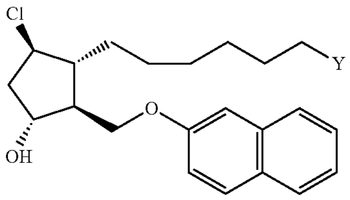

or a pharmaceutically acceptable salt or a prodrug thereof, wherein Y is

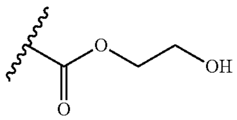
or
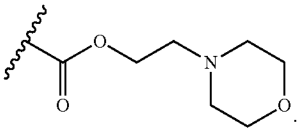

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

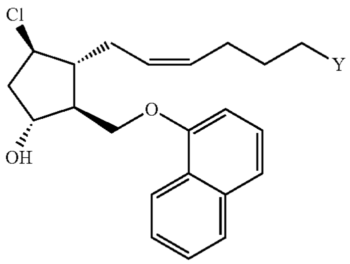

or a pharmaceutically acceptable salt or a prodrug thereof, wherein Y is

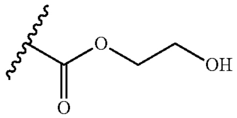
or
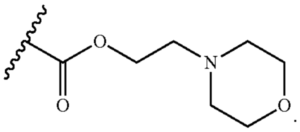

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

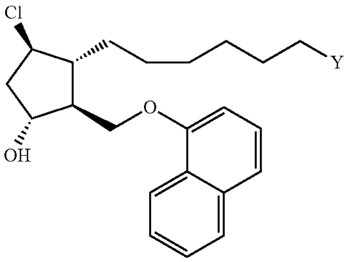

or a pharmaceutically acceptable salt or a prodrug thereof, wherein Y is

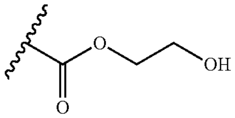
or
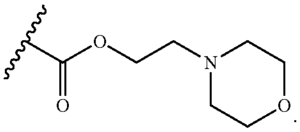

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

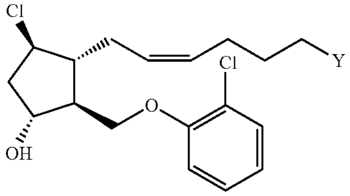

or a pharmaceutically acceptable salt or a prodrug thereof, wherein Y is

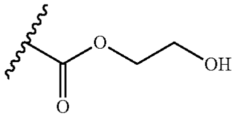

or

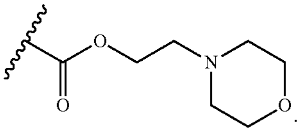

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

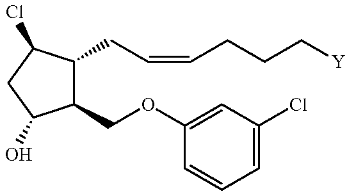

or a pharmaceutically acceptable salt or a prodrug thereof, wherein Y is

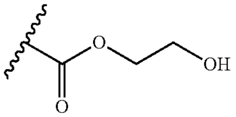

or

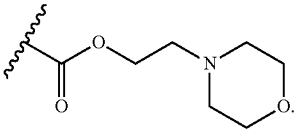

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

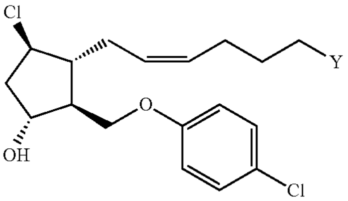

or a pharmaceutically acceptable salt or a prodrug thereof, wherein Y is

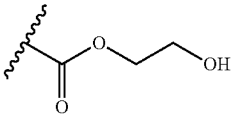

or

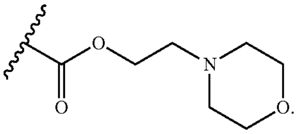

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

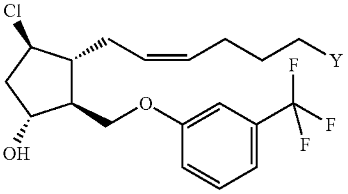

or a pharmaceutically acceptable salt or a prodrug thereof, wherein Y is

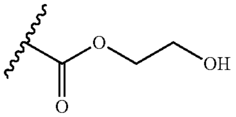
or
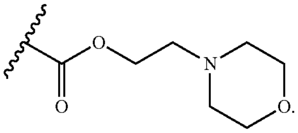

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

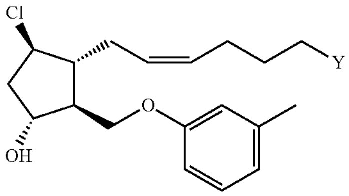

or a pharmaceutically acceptable salt or a prodrug thereof, wherein Y is

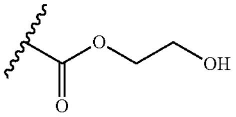
or
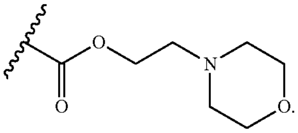

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

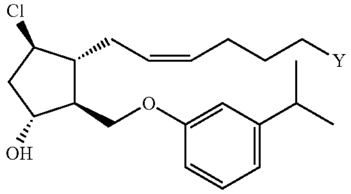

or a pharmaceutically acceptable salt or a prodrug thereof, wherein Y is

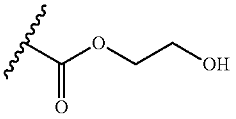
or
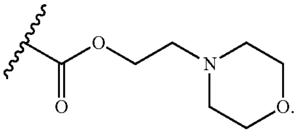

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

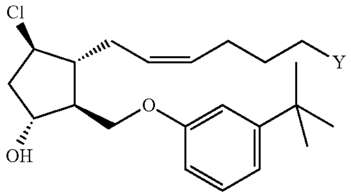

or a pharmaceutically acceptable salt or a prodrug thereof, wherein Y is

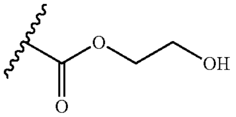
or
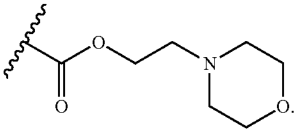

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

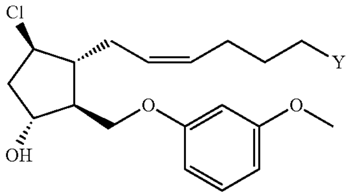

or a pharmaceutically acceptable salt or a prodrug thereof, wherein Y is

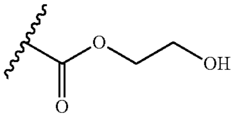

or

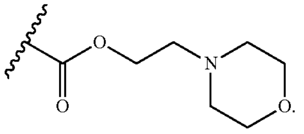

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

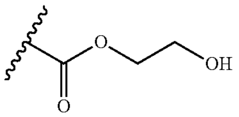

or a pharmaceutically acceptable salt or a prodrug thereof, wherein Y is

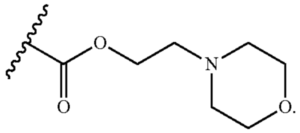

or

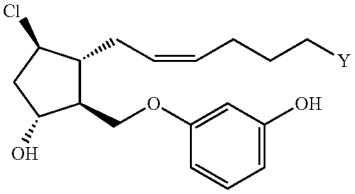

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

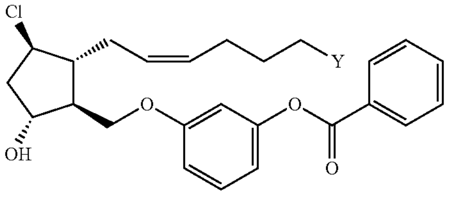

or a pharmaceutically acceptable salt or a prodrug thereof, wherein Y is

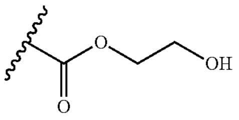

or

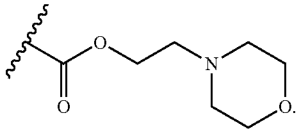

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

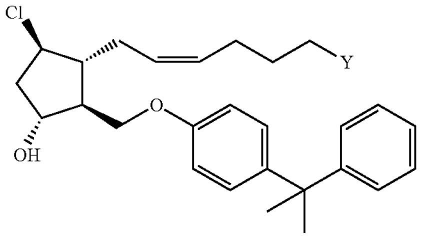

or a pharmaceutically acceptable salt or a prodrug thereof, wherein Y is

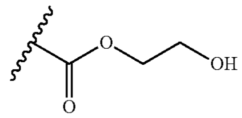

or

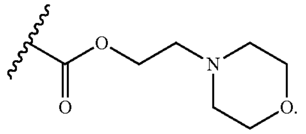

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

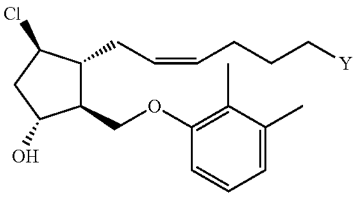

or a pharmaceutically acceptable salt or a prodrug thereof, wherein Y is

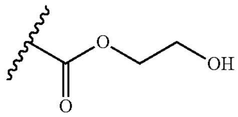

or

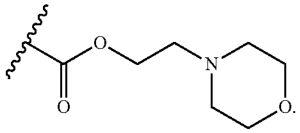

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

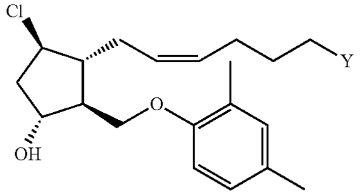

or a pharmaceutically acceptable salt or a prodrug thereof, wherein Y is

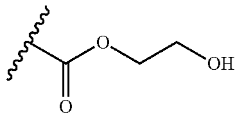

or

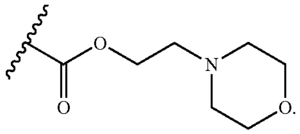

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

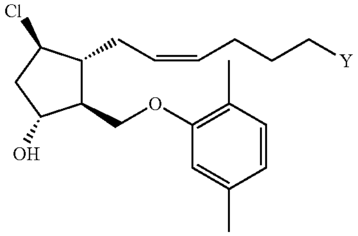

or a pharmaceutically acceptable salt or a prodrug thereof, wherein Y is

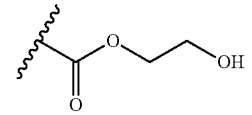

or

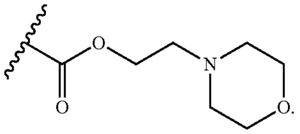

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

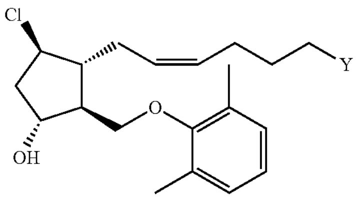

or a pharmaceutically acceptable salt or a prodrug thereof, wherein Y is

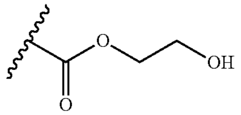

or

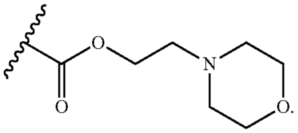

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

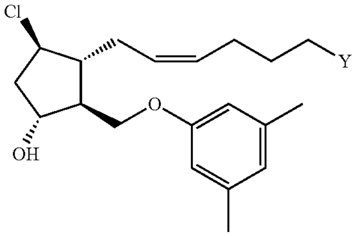

or a pharmaceutically acceptable salt or a prodrug thereof, wherein Y is

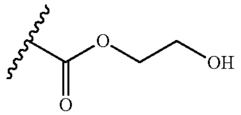

or

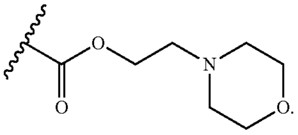

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

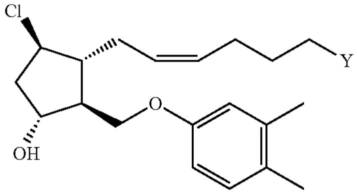

or a pharmaceutically acceptable salt or a prodrug thereof, wherein Y is

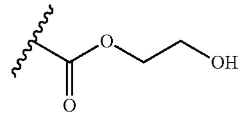

or

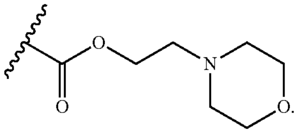

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

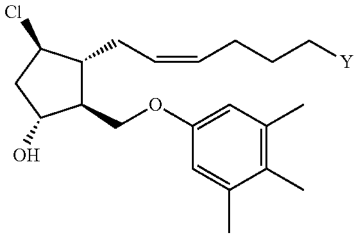

or a pharmaceutically acceptable salt or a prodrug thereof, wherein Y is

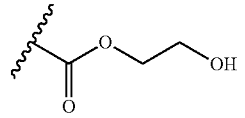

or

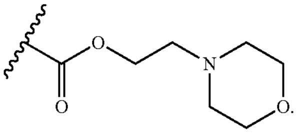

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

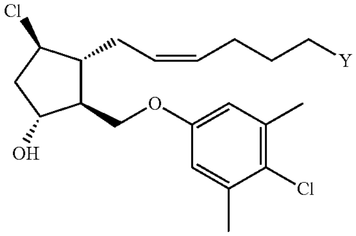

or a pharmaceutically acceptable salt or a prodrug thereof, wherein Y is

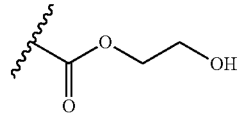

or

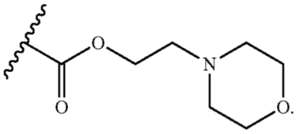

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

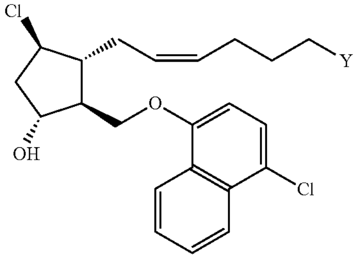

or a pharmaceutically acceptable salt or a prodrug thereof, wherein Y is

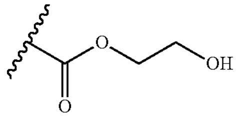

or

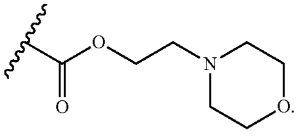

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

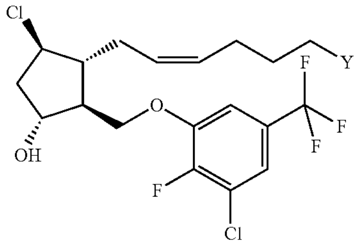

or a pharmaceutically acceptable salt or a prodrug thereof, wherein Y is

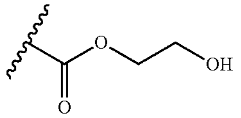

or

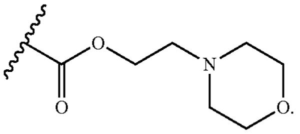

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

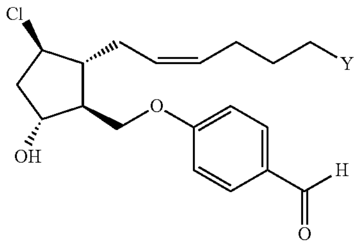

or a pharmaceutically acceptable salt or a prodrug thereof, wherein Y is

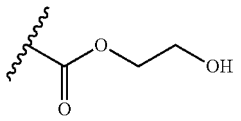

or

-continued

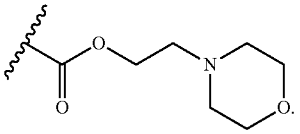

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

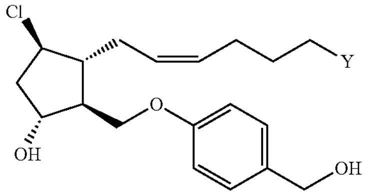

or a pharmaceutically acceptable salt or a prodrug thereof, wherein Y is

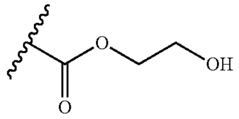

or

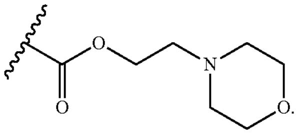

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

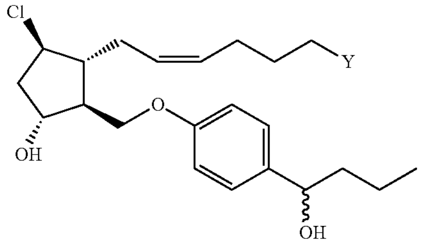

or a pharmaceutically acceptable salt or a prodrug thereof, wherein Y is

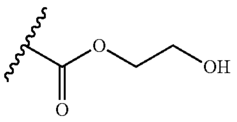

or

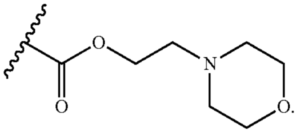

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

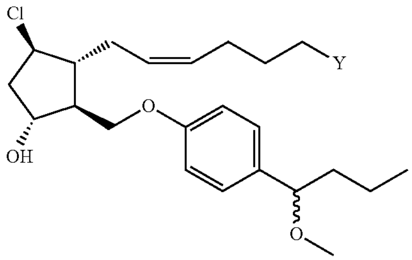

or a pharmaceutically acceptable salt or a prodrug thereof, wherein Y is

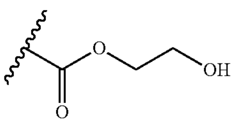

or

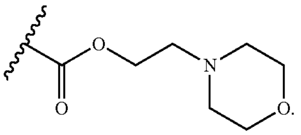

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

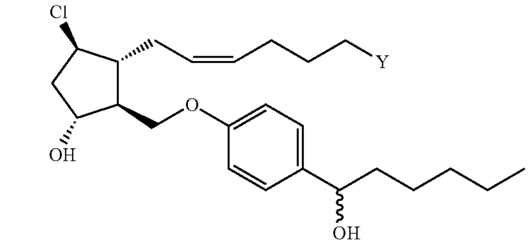

or a pharmaceutically acceptable salt or a prodrug thereof, wherein Y is

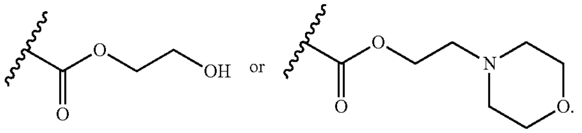 [SMILES: *C(=O)OCCO ; *C(=O)OCCN1CCOCC1]

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

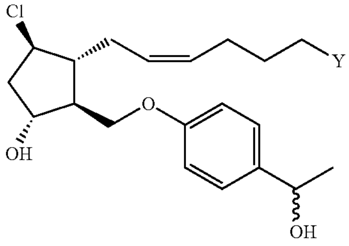

or a pharmaceutically acceptable salt or a prodrug thereof, wherein Y is

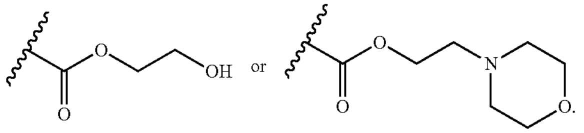 [SMILES: *C(=O)OCCO ; *C(=O)OCCN1CCOCC1]

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

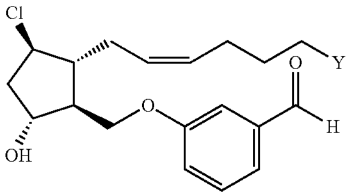

or a pharmaceutically acceptable salt or a prodrug thereof, wherein Y is

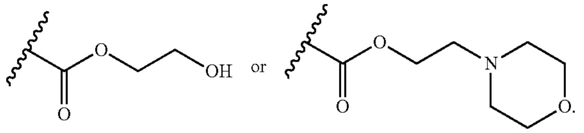 [SMILES: *C(=O)OCCO ; *C(=O)OCCN1CCOCC1]

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

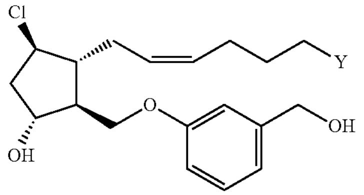

or a pharmaceutically acceptable salt or a prodrug thereof, wherein Y is

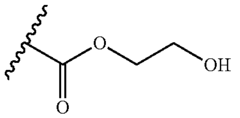

or

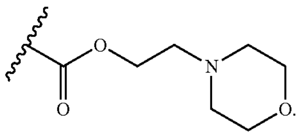

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

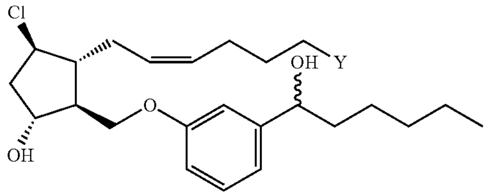

or a pharmaceutically acceptable salt or a prodrug thereof, wherein Y is

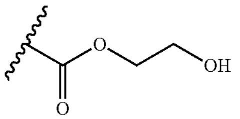

or

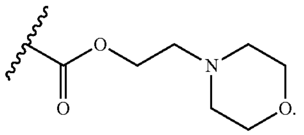

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

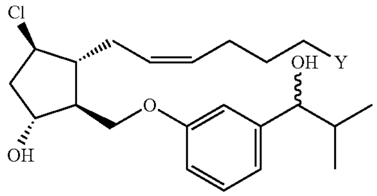

or a pharmaceutically acceptable salt or a prodrug thereof, wherein Y is

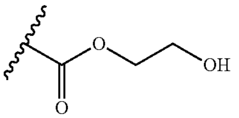

or

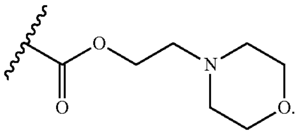

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

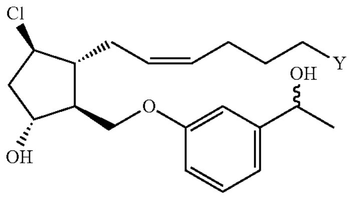

or a pharmaceutically acceptable salt or a prodrug thereof, wherein Y is

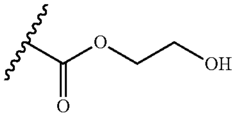
or
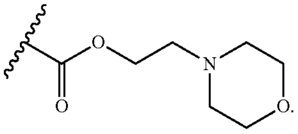

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

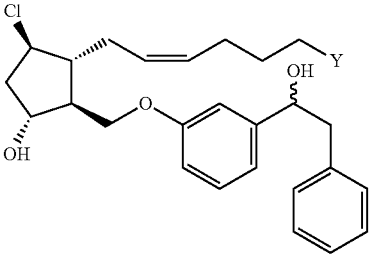

or a pharmaceutically acceptable salt or a prodrug thereof, wherein Y is

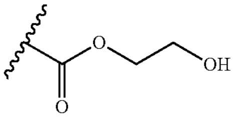
or
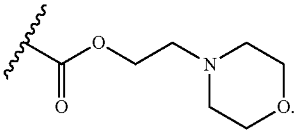

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

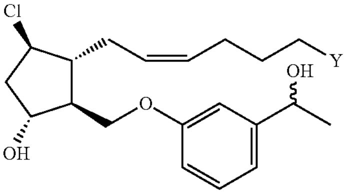

or a pharmaceutically acceptable salt or a prodrug thereof, wherein Y is

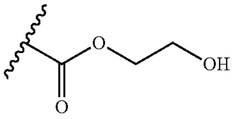
or
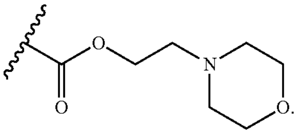

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

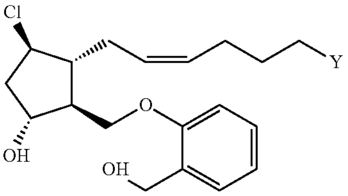

or a pharmaceutically acceptable salt or a prodrug thereof, wherein Y is

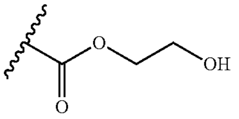
or
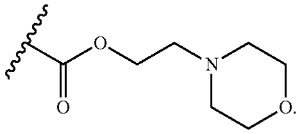

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

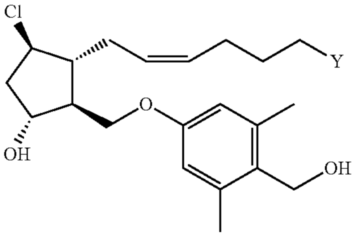

or a pharmaceutically acceptable salt or a prodrug thereof, wherein Y is

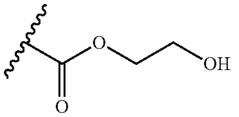
or
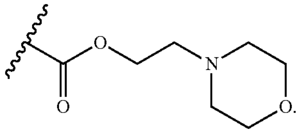

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

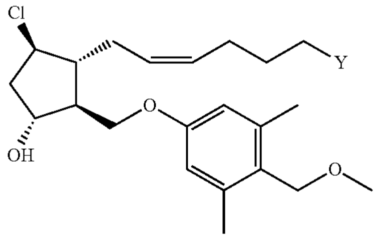

or a pharmaceutically acceptable salt or a prodrug thereof, wherein Y is

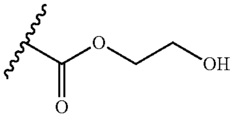
or
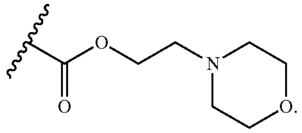

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

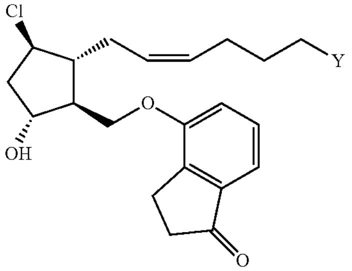

or a pharmaceutically acceptable salt or a prodrug thereof, wherein Y is

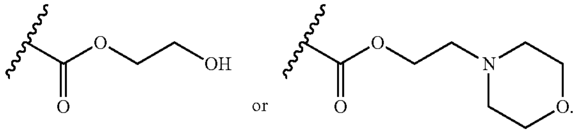 [SMILES: *C(=O)OCCO ; "or" ; *C(=O)OCCN1CCOCC1]

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

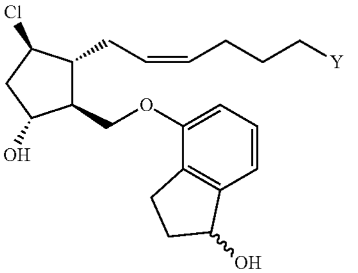

or a pharmaceutically acceptable salt or a prodrug thereof, wherein Y is

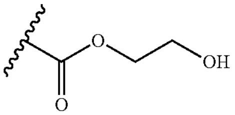

or

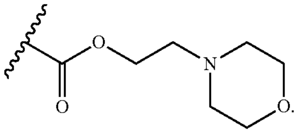

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

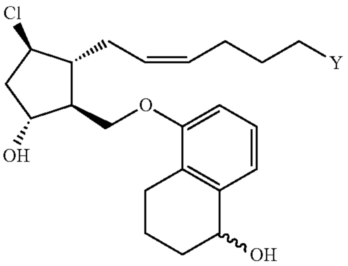

or a pharmaceutically acceptable salt or a prodrug thereof, wherein Y is

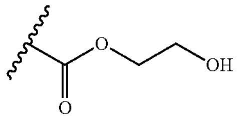

or

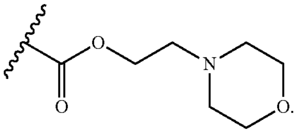

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

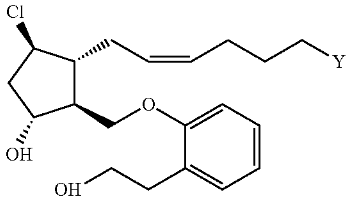

or a pharmaceutically acceptable salt or a prodrug thereof, wherein Y is

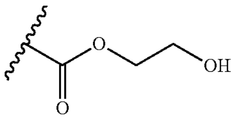
or
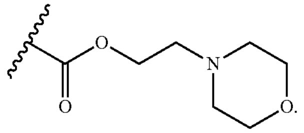

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

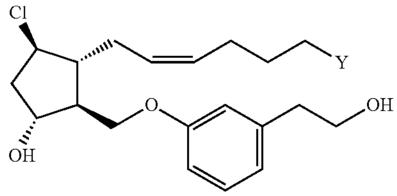

or a pharmaceutically acceptable salt or a prodrug thereof, wherein Y is

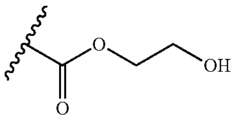
or

-continued

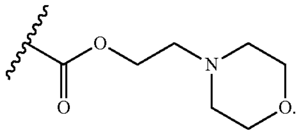

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

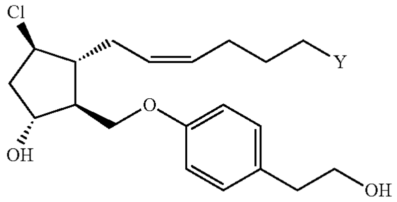

or a pharmaceutically acceptable salt or a prodrug thereof, wherein Y is

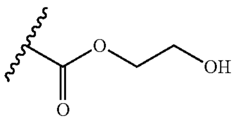
or
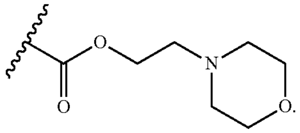

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

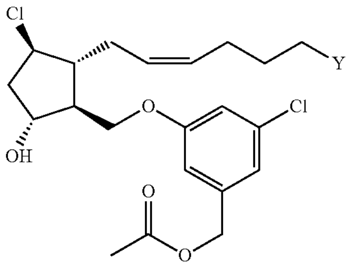

or a pharmaceutically acceptable salt or a prodrug thereof, wherein Y is

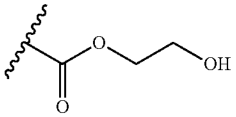

or

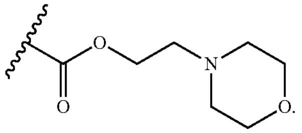

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

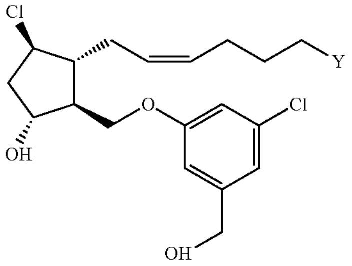

or a pharmaceutically acceptable salt or a prodrug thereof, wherein Y is

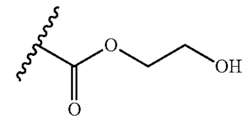

or

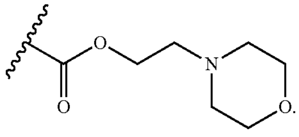

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

Another embodiment is a compound according to the formula

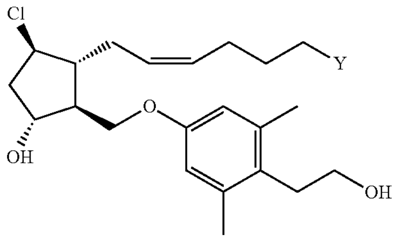

or a pharmaceutically acceptable salt or a prodrug thereof, wherein Y is

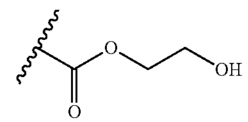

or

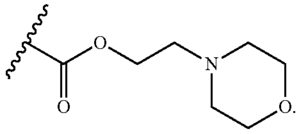

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a composition comprising said compound, and/or salt thereof, and/or prodrug thereof, wherein said composition is used to treat baldness.

The determination of whether a compound is active at a prostaglandin EP2 receptor is well within the ability of a person of ordinary skill in the art. While not intending to limit the scope of the invention in any way, one method of making such a determination is also provided in the examples herein.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

Applications for Stimulating Hair Growth

In one embodiment, the compounds disclosed herein can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The compounds described herein can be used to stimulate, such as the conversion of vellus hair to growth as terminal hair, as well as increasing the rate of growth of terminal hair. The utility of the compounds described herein for the simulation of hair growth was discovered as follows.

In the course of treating patients having glaucoma, treatment may only be appropriate in one eye. Within the course of daily practice, it was discovered that a patient who had been treated with bimatoprost, a prostaglandin analogue, developed lashed that were longer, thicker, and fuller in the treated eye than in the non-treated eye. On examination, the difference was found to be very striking. The lashes were longer and had a fuller, denser appearance in the treated eye. The lash appearance on the lids of the treated eyes would have appeared quite attractive if it represented a bilateral phenomenon. As a result of its asymmetric nature, the long lashes on one side could be construed as disturbing from a cosmetic standpoint. A systemic examination was preformed as a result of the asymmetric phenomenon. It soon became apparent that this altered appearance was not an isolated finding. Comparison of the lids of patients who were taking bimatoprost in only one eye revealed subtle changes in the lashed and adjacent hairs of the bimatoprost-treated side in several patients. Definite differences could be identified to varying degrees in the lashes and adjacent hairs of all patients who were taking the drug on a unilateral basis for longer than 6 months.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of glaucoma follow-up examination, attention is generally immediately focused on the eye itself. As a result of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treatment area following administration of the prostaglandin analogue were multiple. They included increased length of lashed, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation of lashes and lash-like terminal hairs. The conclusion that hair growth is stimulated by prostaglandin analogues such as bimatoprost is thus supported not by evidence of a difference in a single parameter, but is based on multiple parameters of hair appearance in treated versus control areas in many subjects.

The compounds described herein are prostaglandin analogues and therefore have similar activities as bimatoprost, contain structural similarities, and therefore are expected to stimulate hair growth and stimulation of the conversion of vellus hair to terminal hair. In one embodiment, the compounds described herein and their prodrugs can be used for the stimulation of hair growth. As used herein, hair growth includes hair associated with the scalp, eyebrows, eyelids, beard, and other areas of the skin of animals.

In one embodiment, the compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more compounds as defined above and a dermatologically compatible carrier. Effective amounts of the active compounds may be determined by one of ordinary skill in the art, but will vary depending on the compound employed, frequency of application and desired result. The compound will generally range from about 0.0000001 to about 50% by weight of the dermatological composition. Preferably, the compound will range from about 0.001 to about 50% by weight of total dermatological composition, more preferably from about 0.1 to about 30% by weight of the composition.

In one embodiment, the application of the present compounds for stimulation of hair growth finds applications in mammalian species, including both humans and animals. In humans, the compounds described herein can be applied for example, to the scalp, face beard, head, pubic area, upper lip, eyebrows, and eyelids. In animal raised for their pelts, e.g., mink, the compounds described herein can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably, at least six months.

For topical use on the eyelids or eyebrows, the active compounds can be formulated in aqueous solutions, creams, ointments, or oils exhibiting physiological acceptable osmolarity by addition of pharmaceutically acceptable buffers and salts. such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matricies may also be employed as well as soluble and insoluble ocular inserts, for instance, based on substances forming in situ gels. Depending on the actual formation and compound to be used, various amounts of the drug and different dose regimens may be employed. Typically, the daily amount of compound for treatment of the eyelid may be about 0.1 ng to about 100 mg per eyelid.

For topical use on the skin and scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matricies for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs is contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and $\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including

- direct acting cholinergic agonists such as charbachol, pilocarpine hydrochloride, pilocarbine nitrate, pilocarpine, and the like, or pharmaceutically acceptable salts or prodrugs thereof;
- chlolinesterase inhibitors such as demecarium, echothiophate, physostigmine, and the like, or pharmaceutically acceptable salts or prodrugs thereof;

Glutamate Antagonists such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chloprostenol, fluprostenol, 13,14-dihydro-chloprostenol, latanoprost and the like.

The following compounds can be useful according to the present description:

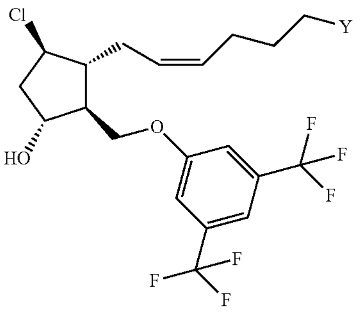

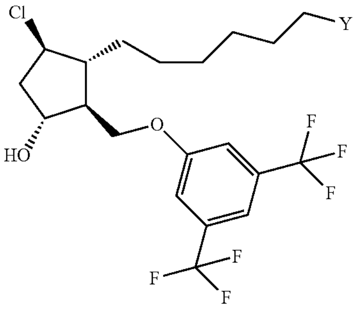

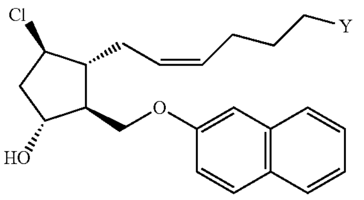

-continued

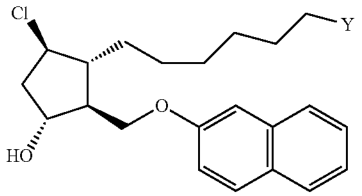

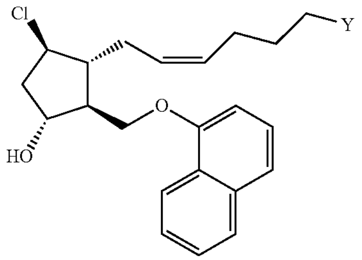

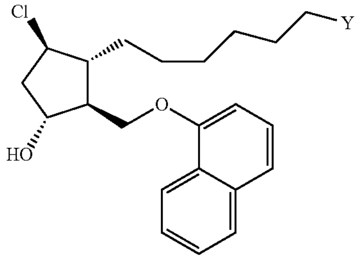

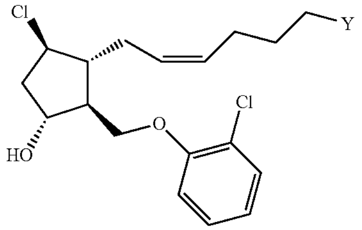

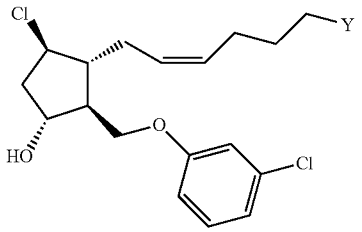

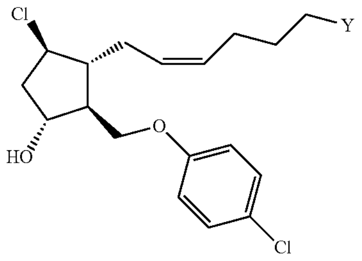

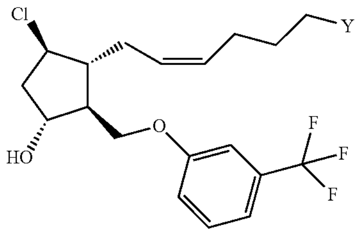

-continued
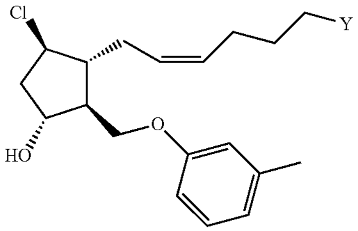
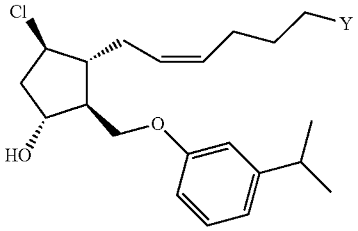
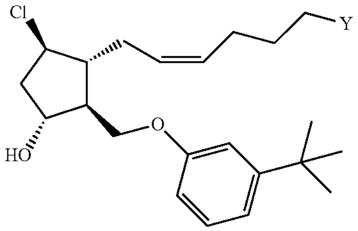
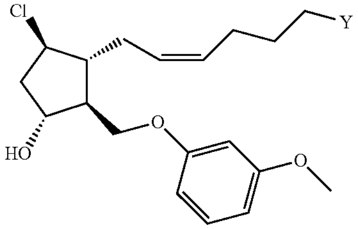
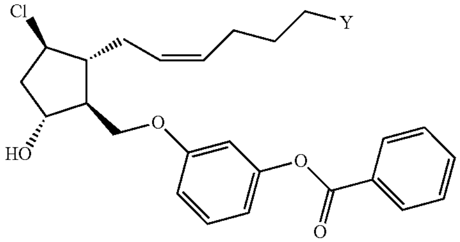
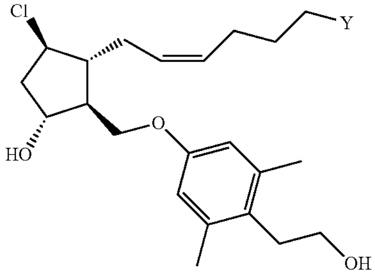
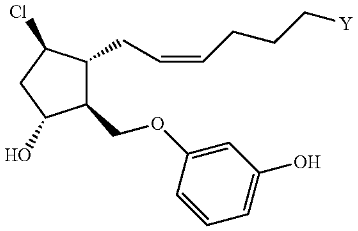
-continued
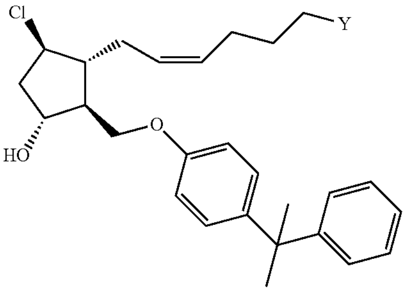
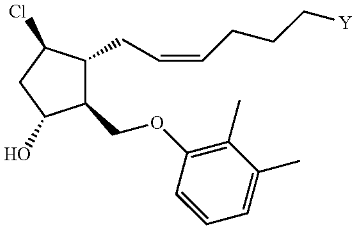
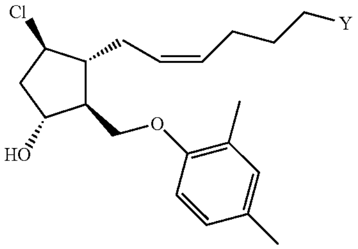
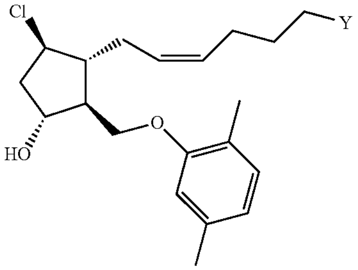
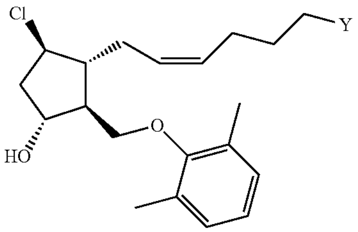
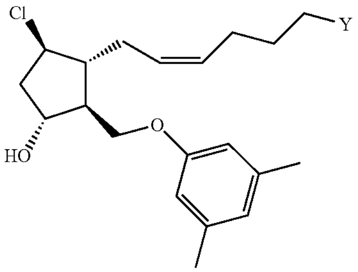

-continued
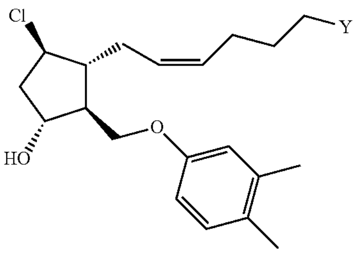
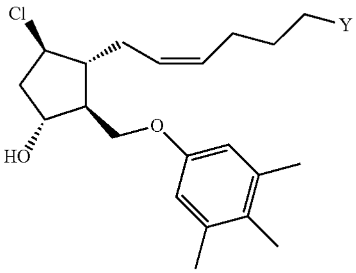
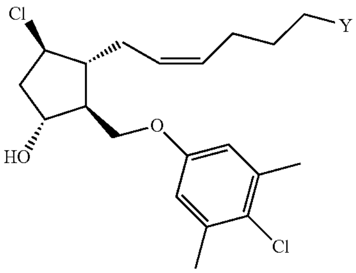
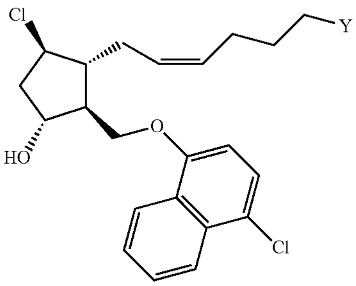
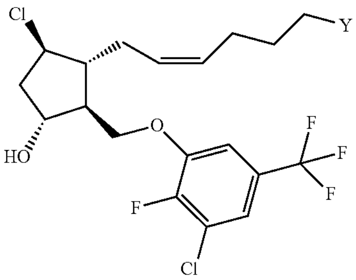
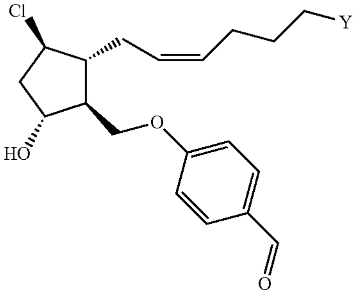
-continued
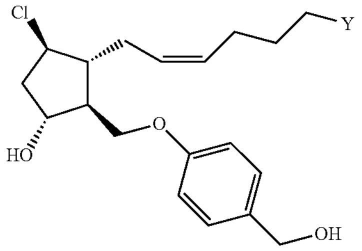
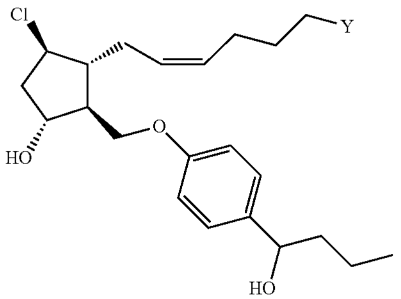
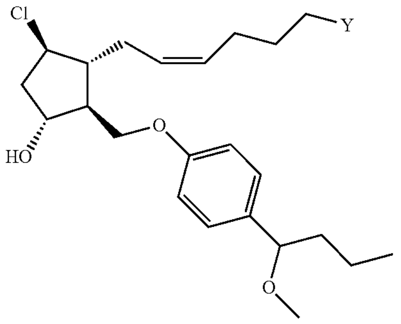
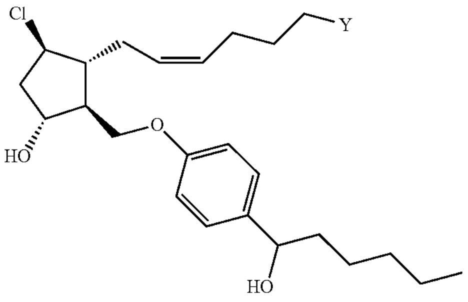
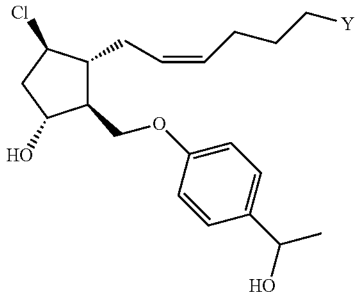
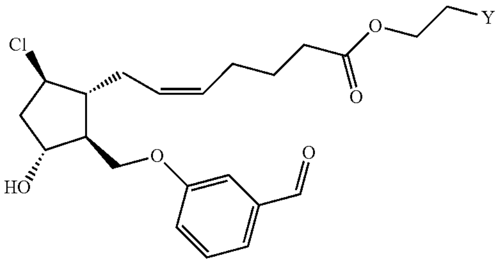

-continued
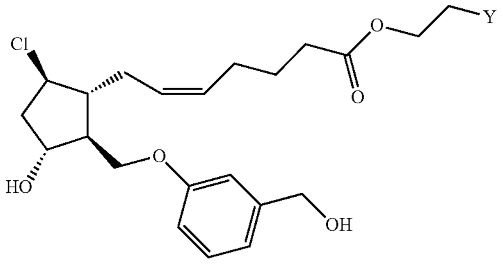
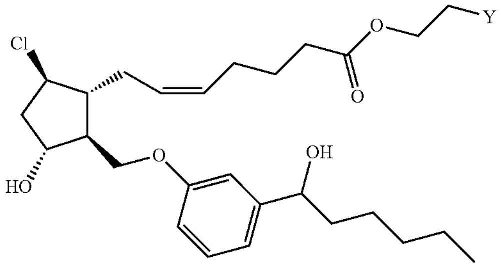
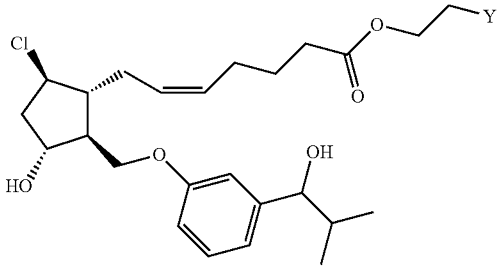
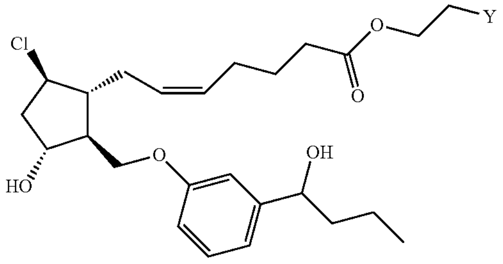
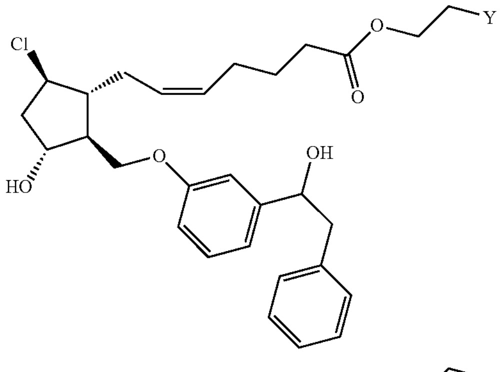
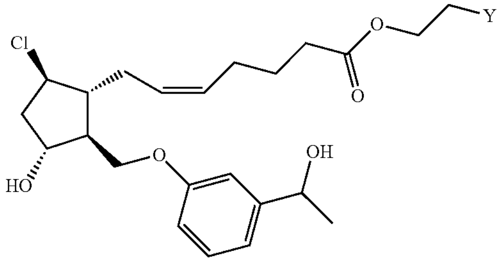
-continued
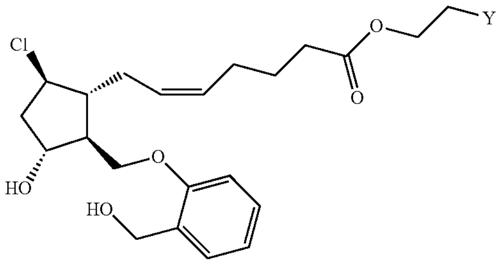
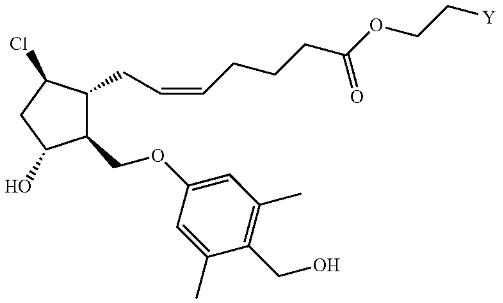
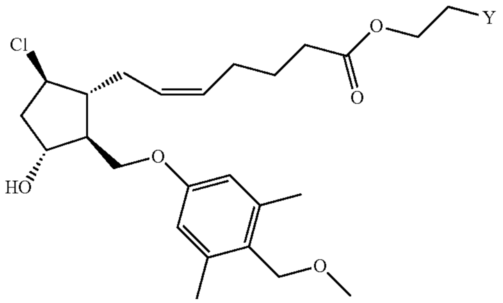
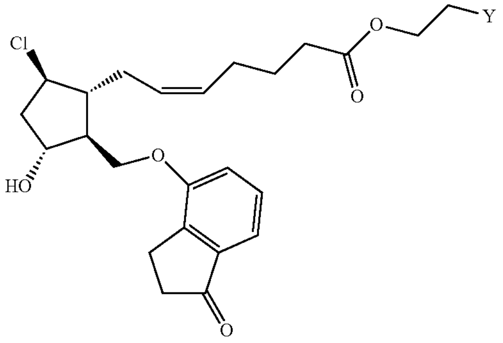
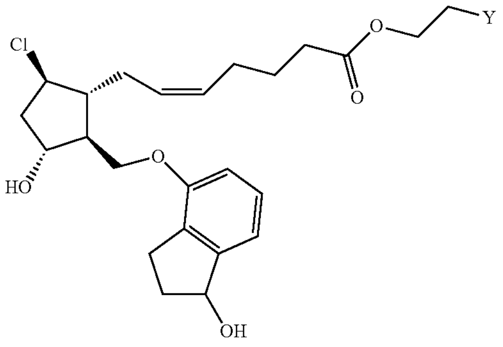

-continued
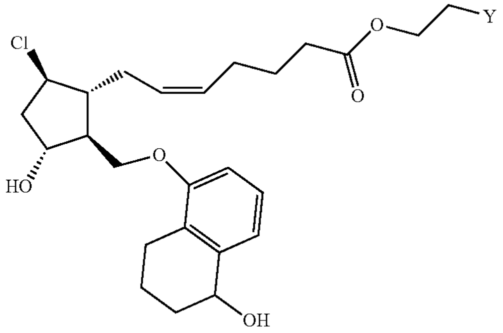
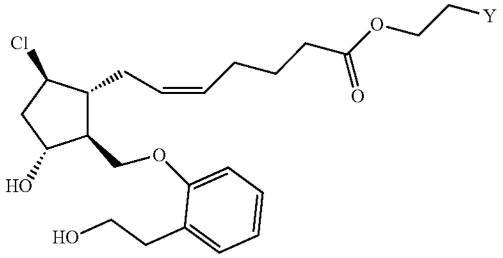
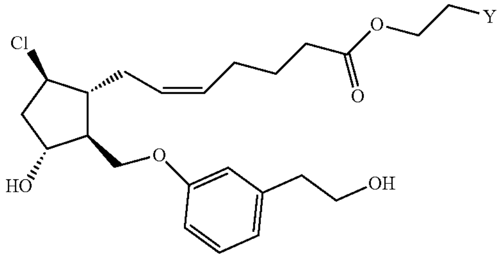
-continued
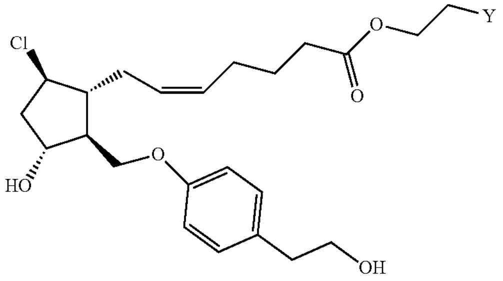
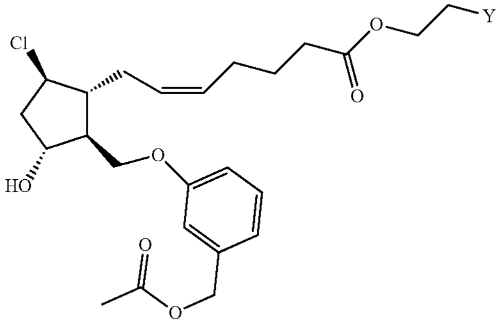
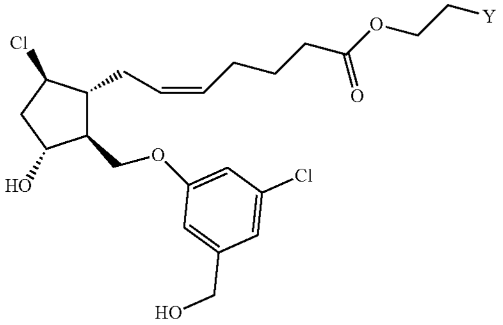
EXAMPLES
Scheme 1
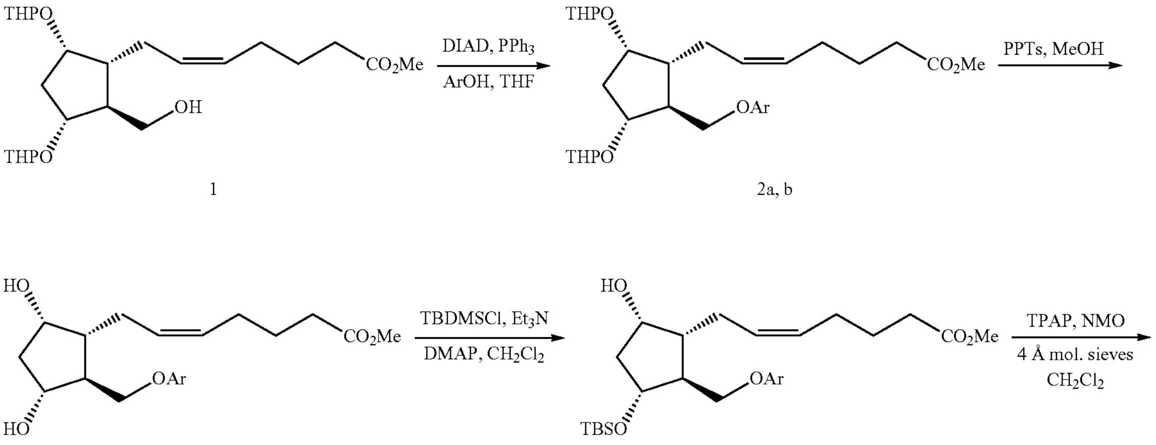
3a, b
4a, b -continued

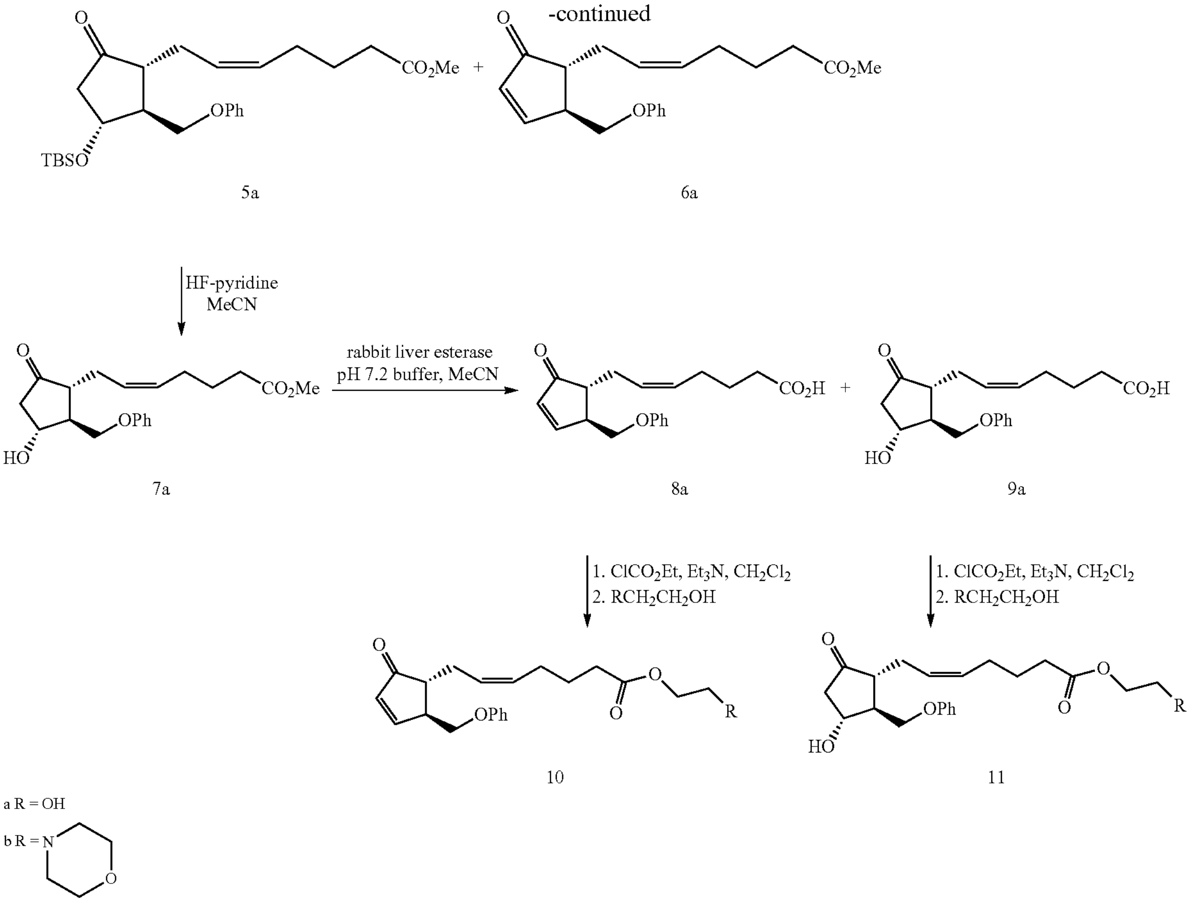

5a 6a 7a 8a 9a 10 11

Example 1

Step 1: Mitsonobu Reaction of Phenol and 1 to give 2a.

A solution of diisopropyl azodicarboxylate (DIAD, 194 μL, 1.0 mmol) in THF (1.5 mL) was added to a solution of alcohol 1 (441 mg, 1.0 mmol), triphenylphosphine (262 mg, 1.0 mmol) and phenol (94 mg, 1.0 mmol) in THF (3.0 mL). After stirring 18 h at room temperature, the solvent was removed under a stream of nitrogen and the residue was suspended in $Et_2O$ (50 mL). The mixture was washed with saturated aqueous $NaHCO_3$ (3×20 mL) and brine (20 mL) then the organic phase was dried ($Na_2SO_4$) filtered and concentrated in vacuo. Purification of the residue by flash column chromatography on silica gel (hexane→50% EtOAc/hexane, gradient) afforded 218 mg of the desired ether 2a contaminated with phenol (approximately 15% phenol by $^1H$ NMR analysis) which was taken on without further purification.

Step 2: Deprotection of 2a to Give 3a.

Pyridinium p-toluenesulfonate (PPTs, 9 mg, 0.036 mmol) was added to a solution of impure 2a (218 mg, ~0.36 mmol) in methanol (3.6 mL) at room temperature under nitrogen. The solution was heated at 50° C. for 4 h, then cooled and concentrated in vacuo. Purification of the crude residue by flash column chromatography on silica gel (60% EtOAc/hexane→EtOAc, gradient) afforded 112 mg (32% over two steps) of diol 3a.

Step 3: Silylation of 3a to Give 4a.

Triethylamine (67 μL, 0.48 mmol), dimethylaminopyridine (8 mg, 0.065 mmol), and tert-butyldimethylsilyl chloride (54 mg, 0.36 mmol) were sequentially added to a solution of 3a (112 mg, 0.32 mmol) in $CH_2Cl_2$ (1.6 mL). The resulting solution was stirred at room temperature under nitrogen for 18 h. The reaction mixture was then concentrated in vacuo, then saturated aqueous $NH_4Cl$ (20 mL) was added and the mixture was extracted with EtOAc (3×30 mL). The combined organic extracts were washed with brine (20 mL), dried ($Na_2SO_4$), filtered and concentrated in vacuo. Purification of the crude residue by flash column chromatography on silica gel (25%→60% EtOAc/hexane→EtOAc, gradient) afforded 96 mg (65%) of desired product 4a.

Step 4: Oxidation of 4a to Give 5a.

4-Methylmorpholine N-oxide (17.5 mg, 0.15 mmol) and 4 Å molecular sieves (25 mg) were added to a solution of 4a (46 mg, 0.10 mmol) in $CH_2Cl_2$ (0.5 mL). The mixture was cooled to 0° C. and tetrapropylammonium perruthenate (TPAP, 1.8 mg, 0.005 mmol) was added in one portion. The reaction mixture was allowed to warm to room temperature. After 18 h at room temperature the reaction was concentrated in vacuo. Purification of the crude residue by flash column chromatography on silica gel (15%→60% EtOAc/hexane) afforded 27 mg (59%) of 5a and 6 mg (18%) of compound 6a.

Step 5: Conversion of 5a to 7a

HF-pyridine (100 μL) was added to a solution of 5a (27 mg, 0.059 mmol) in $CH_3CN$ (1.2 mL) in a plastic scintillation vial at room temperature. After 18 h, the reaction was quenched with saturated aqueous $NaHCO_3$ (10 mL) and extracted with EtOAc (3×15 mL). The combined organic extracts were dried ($Na_2SO_4$), filtered and concentrated in vacuo. Purification of the crude residue by flash column chromatography on silica gel (40% EtOAc/hexane) afforded 9 mg (44%) of compound 7a.

Step 6: Conversion of 5a to 7a

Rabbit liver esterase (134 units/mg, 1 mg) was added to a solution of 7a (5.0 mg, 0.022 mmol) in MeCN (0.1 mL) and pH 7.2 buffer (0.72 mL). After stirring at room temperature for 18 h, the reaction mixture was diluted with MeCN (5 mL) and concentrated to dryness. The residue was suspended in $CH_2Cl_2$, filtered through celite and concentrated. Purification of the resulting crude residue by flash column chromatography on silica gel (70% EtOAc/hexane→EtOAc→2% MeOH/EtOAc, gradient) afforded 0.9 mg (20%) of compound 8a and 3.0 mg (63%) of compound 9a.

Step 7: Conversion of 8a to 10a and 10b

Triethylamine and ethyl chloroformate are added sequentially to a solution of compound 8a in $CH_2Cl_2$ at room temperature. After 2.5 h, triethylamine and ethylene glycol are added. After stirring overnight at room temperature, the reaction mixture is partitioned between $H_2O$ and $CH_2Cl_2$. The phases are separated and the aqueous phase is extracted with $CH_2Cl_2$ (2×). The combined organic phase is washed with 1 N HCl then dried ($MgSO_4$), filtered and concentrated in vacuo. Purification of the residue by flash column chromatography on silica gel (10% $CH_3OH/CH_2Cl_2$) affords compound 10a.

Triethylamine and ethyl chloroformate are added sequentially to a solution of compound 8a in $CH_2Cl_2$ at room temperature. After 2.5 h, triethylamine and 4-(2-hydroxyethyl)-morphine are added. After stirring overnight at room temperature, the reaction mixture is partitioned between $H_2O$ and $CH_2Cl_2$. The phases are separated and the aqueous phase is extracted with $CH_2Cl_2$ (2×). The combined organic phase is washed with 1 N HCl then dried ($MgSO_4$), filtered and concentrated in vacuo. Purification of the residue by flash column chromatography on silica gel (10% $CH_3OH/CH_2Cl_2$) affords compound 10b.

Step 8: Conversion of 9a to 11a and 11b

Triethylamine and ethyl chloroformate are added sequentially to a solution of compound 9a in $CH_2Cl_2$ at room temperature. After 2.5 h, triethylamine and ethylene glycol are added. After stirring overnight at room temperature, the reaction mixture is partitioned between $H_2O$ and $CH_2Cl_2$. The phases are separated and the aqueous phase is extracted with $CH_2Cl_2$ (2×). The combined organic phase is washed with 1 N HCl then dried ($MgSO_4$), filtered and concentrated in vacuo. Purification of the residue by flash column chromatography on silica gel (10% $CH_3OH/CH_2Cl_2$) affords compound 11a.

Triethylamine and ethyl chloroformate are added sequentially to a solution of compound 9a in $CH_2Cl_2$ at room temperature. After 2.5 h, triethylamine and 4-(2-hydroxyethyl)-morphine are added. After stirring overnight at room temperature, the reaction mixture is partitioned between $H_2O$ and $CH_2Cl_2$. The phases are separated and the aqueous phase is extracted with $CH_2Cl_2$ (2×). The combined organic phase is washed with 1 N HCl then dried ($MgSO_4$), filtered and concentrated in vacuo. Purification of the residue by flash column chromatography on silica gel (10% $CH_3OH/CH_2Cl_2$) affords compound 11b.

Example 2

Scheme 2

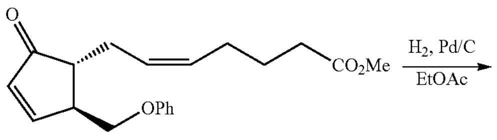

6a

-continued

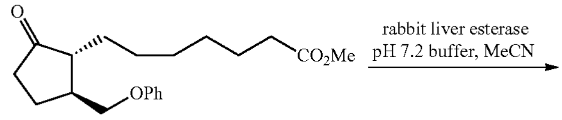

12

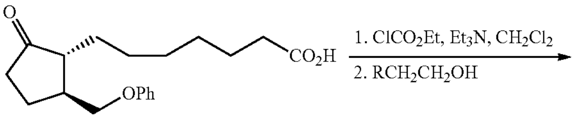

13

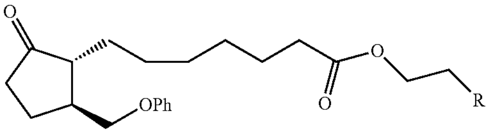

14 a R = OH b R = 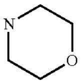

Step 1: Conversion of 6a to 12

Palladium on carbon (10 wt. %, 3 mg) was added to a solution of 6a (9.0 mg, 0.027 mmol) in EtOAc (0.65 mL). A hydrogen atmosphere was established by evacuating and refilling with hydrogen (3×) and the reaction mixture was stirred under a balloon of hydrogen for 18 h. The reaction mixture was filtered through celite, washing with EtOAc, and the filtrate was concentrated in vacuo to afford 7.5 mg (82%) of compound 12.

Step 2: Conversion of 12 to 13

Compound 12 (6.5 mg, 0.020 mmol) was converted to compound 13 (4.0 mg (64%)) in accordance with the procedure in Examples 1, Step 7.

Step 3: Conversion of 13 to 14a and 14b

Compound 13 is converted to compound 14a and 14b in accordance with the procedure in Examples 1, Step 8.

Example 3

Scheme 3

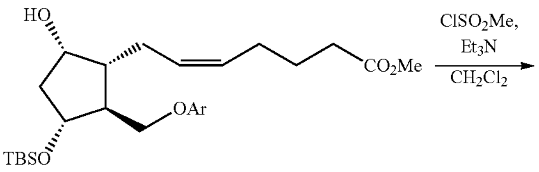

4a, b

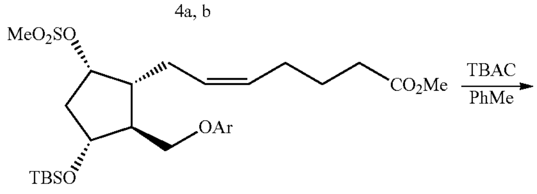

15

-continued

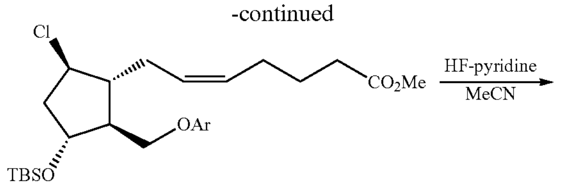

16

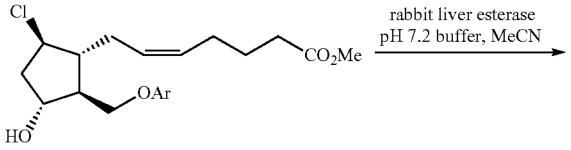

17

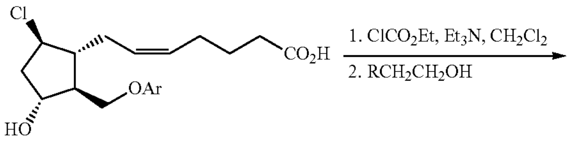

18

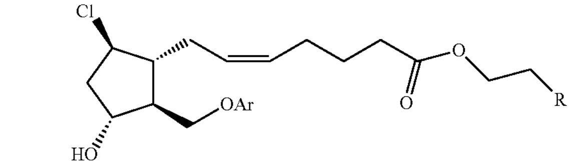

19 a R = OH b R = 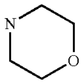

Step 1: Mesylation of 4a to Give 15.

Triethylamine (23 µL, 0.17 mmol) and methanesulfonyl chloride (11 µL, 0.14 mmol) were added sequentially to a solution of 4a (51 mg, 0.11 mmol) in $CH_2Cl_2$ (0.8 mL) at room temperature. After 18 h at room temperature, saturated aqueous $NaHCO_3$ (5 mL) was added and the mixture was extracted with EtOAc (3x10 mL). The combined organic extracts were dried ($Na_2SO_4$), filtered and concentrated in vacuo. Purification of the crude residue by flash column chromatography on silica gel (25% EtOAc/hexane) afforded 47 mg (79%) of 15.

Step 2: Conversion of 15 to chloride 16.

Tetrabutylammonium chloride (250 mg, 0.90 mmol) was added to a solution of 15 (47 mg, 0.087 mmol) in toluene (2.9 mL). The reaction mixture was heated at 50° C. for 18 h. The cooled mixture was diluted with brine (10 mL) and extracted with EtOAc (3x25 mL). The combined organic extracts were dried ($Na_2SO_4$), filtered and concentrated in vacuo. Purification of the crude residue by flash column chromatography on silica gel (15% EtOAc/hexane) afforded 32 mg (77%) of 16.

Step 3. Deprotection of 16 to Give 17.

HF-pyridine (100 µL) was added to a solution of 16 (27 mg, 0.059 mmol) in $CH_3CN$ (1.3 mL) in a plastic scintillation vial at room temperature. After 18 h, the reaction was quenched with saturated aqueous $NaHCO_3$ (10 mL) and extracted with EtOAc (3x15 mL). The combined organic extracts were dried ($Na_2SO_4$), filtered and concentrated in vacuo. Purification of the crude residue by flash column chromatography on silica gel (25% EtOAc/hexane) afforded 20 mg (82%) of compound 17.

Step 4. Conversion of 17 to give 18.

Compound 17 is converted to compounds 18 in accordance with the procedure in Examples 1, Step 7.

Step 5. Conversion of 18 to give 19a and 19b.

Compound 18 is converted to compounds 19a and 19b in accordance with the procedure in Examples 1, Step 8.

Example 4

Scheme 4

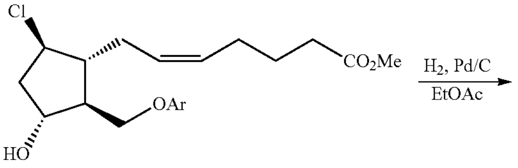

17

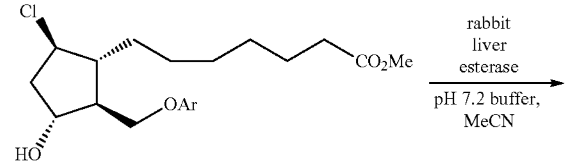

20

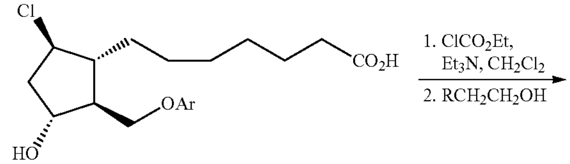

21

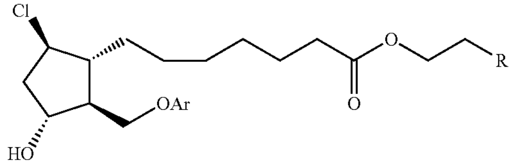

22 a R = OH b R = 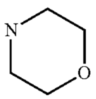

Step 1. Conversion of 17 to 20.

Palladium on carbon (10 wt. %, 3 mg) was added to a solution of 17 (9.0 mg, 0.027 mmol) in EtOAc (0.7 mL). A hydrogen atmosphere was established by evacuating and refilling with hydrogen (5x) and the reaction mixture was stirred under a balloon of hydrogen for 18 h. The reaction mixture was filtered through celite, washing with EtOAc, and the filtrate was concentrated in vacuo to afford 9.0 mg (quant.) of compound 20.

Step 2. Conversion of 20 to 21.

Compound 20 (16a, 8.0 mg, 0.021 mmol) was converted to compound 21 (2.0 mg (26%)) in accordance with the procedure in Example 1, Step 7.

Step 3: Conversion of 21 to 22a and 2b

Compound 21 is converted to compound 22a and 22b in accordance with the procedure in Examples 1, Step 8.

Example 5

Scheme 5

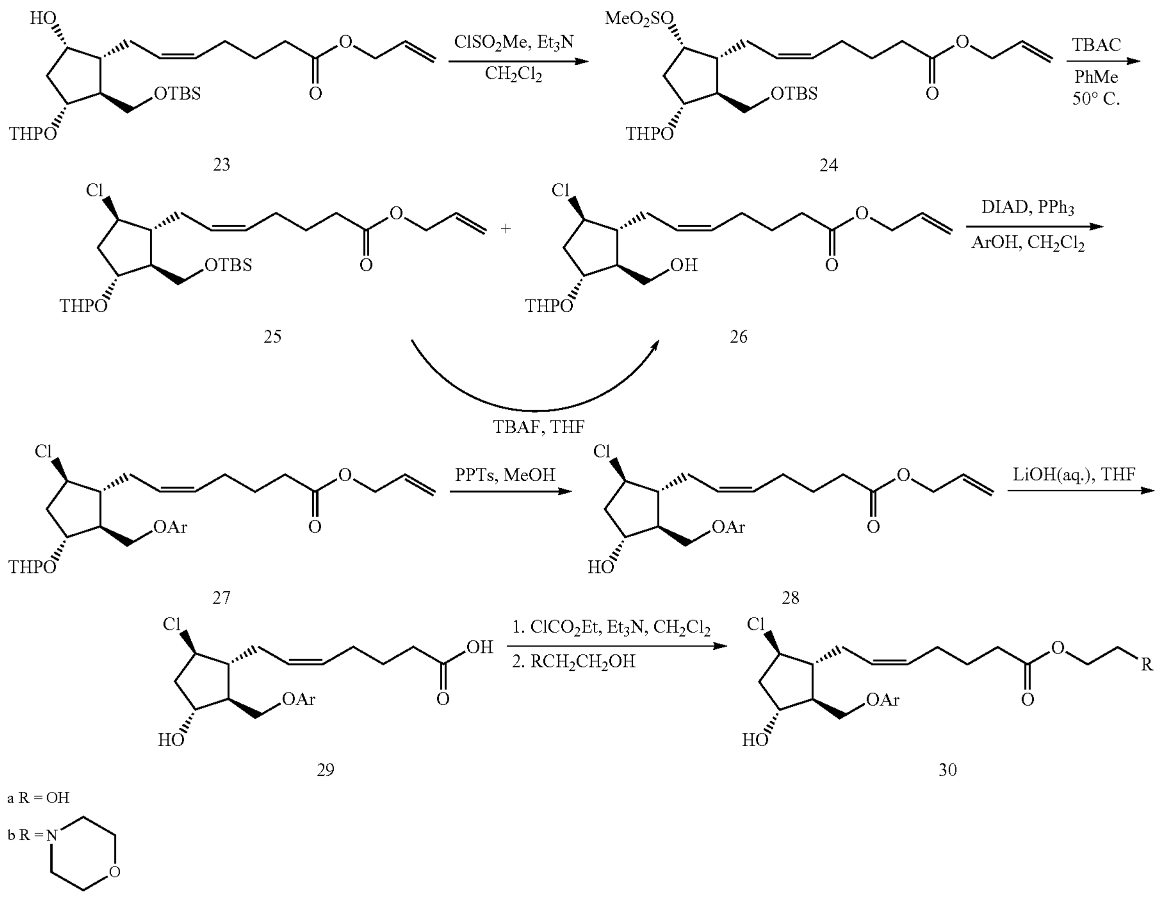

Step 1: Mesylation of 23 to Give 24

Triethylamine (4.2 mL, 30 mmol) and methanesulfonyl chloride (1.9 mL, 24 mmol) were added sequentially to a solution of (Z)-7-[(1R,2S,3R,5S)-2-(tert-butyl-dimethyl-silanyloxymethyl)-5-hydroxy-3-(tetrahydro-pyran-2-yloxy)-cyclopentyl]-hept-5-enoic acid allyl ester (23, 9.94 g, 20 mmol) in $CH_2Cl_2$ (150 mL) at 0° C. The reaction mixture was allowed to warm to room temperature. After 18 h at room temperature, the reaction mixture was added to saturated aqueous $NaHCO_3$ (200 mL) and $CH_2Cl_2$ was removed in vacuo. The resulting aqueous mixture was extracted with EtOAc (3×300 mL). The combined extracts were washed with brine (100 mL), dried ($Na_2SO_4$), filtered and concentrated in vacuo to afford 11.5 g (quant.) of mesylate 24 as a pale yellow oil.

Step 2: Conversion of 24 to Chlorides 25 and 26

A mixture of 24 (1.73 g, 3.01 mmol) and tetrabutylammonium chloride (8.4 g, 30.2 mmol) in toluene (100 mL) was stirred at 50° C. After 18 h, the reaction was cooled to room temperature and brine (150 mL) was added. The mixture was extracted with EtOAc (3×200 mL). The combined extracts were washed with brine (150 mL), dried ($Na_2SO_4$), filtered and concentrated in vacuo. Purification of the crude residue by flash column chromatography on silica gel (10%→25%→50% EtOAc/hexane, gradient) afforded 695 mg (45%) of chloride 25 along with 223 mg (18%) of compound 26.

Step 3: Deprotection of 25 to Give 26

Tetrabutylammonium fluoride (4.0 mL of a 1.0 M THF solution, 4.0 mmol) was added to a solution of 25 (695 mg, 1.35 mmol) in THF (5.4 mL) at 0° C. under $N_2$. The reaction mixture was allowed to warm to room temperature. After 18 h at room temperature, THF was removed under a stream of $N_2$. EtOAc (100 mL) was added and the resulting mixture was washed with $H_2O$ (2×50 mL) and brine (50 mL) then dried ($Na_2SO_4$), filtered and concentrated in vacuo. Purification of the crude residue by flash column chromatography on silica gel (30% EtOAc/hexane) afforded 392 mg (72%) of compound 26 as a colorless oil.

Step 4: Mitsunobu Reaction of 26 and Hydroxyaryl to Give 27.

DIAD (50 μL, 0.26 mmol) was added to a solution of alcohol 26 (88 mg, 0.22 mmol), triphenylphosphine (88 mg, 0.34 mmol) and 3,5-bis(trifluoromethyl)phenol (40 μL, 0.26 mmol) in $CH_2Cl_2$ (1.1 mL). After stirring overnight at room temperature, the solvent was removed under a stream of nitrogen. The residue was diluted with EtOAc (25 mL), washed with saturated aqueous $NaHCO_3$ (3×10 mL) and brine (10 mL) then the organic phase was dried ($Na_2SO_4$) filtered and concentrated in vacuo. Purification of the residue by flash column chromatography on silica gel (10% EtOAc/hexane) afforded 112 mg (83%) of the desired ether 27.

Step 5: Deprotection of 27 to Give 28.

Pyridinium p-toluenesulfonate (PPTs, 5 mg, 0.019 mmol) was added to a solution of 27 (112 mg, 0.18 mmol) in methanol (1.8 mL) at room temperature under nitrogen. The solution was heated at 50° C. overnight, then cooled and concentrated in vacuo. Purification of the crude residue by flash column chromatography on silica gel (25% EtOAc/hexane→EtOAc, gradient) afforded 24 mg (25%) of pure 27 and 67 mg (~70%) of 27 contaminated with ~10% of a slightly more polar impurity.

Step 6: Saponification of 27 to Give 28.

Lithium hydroxide (0.05 mL of a 1.0 M aqueous solution, 0.05 mmol) was added to a solution of ester 27 (9 mg, 0.017 mmol) in THF (0.17 mL). After stirring overnight at room temperature, the solvent was removed under a stream of nitrogen. $H_2O$ (2 mL) was added, the mixture was acidified with 1.0 M aqueous HCl (0.5 mL), and the resulting cloudy solution was extracted with EtOAc (3×10 mL). The combined extracts were washed with brine (10 mL), dried ($Na_2SO_4$), filtered and concentrated in vacuo to afford 8 mg (96%) of compound 28.

Step 7: Conversion of 28 to 29a and 29b

Compound 28 is converted to compound 29a and 29b in accordance with the procedure in Examples 1, Step 8.

Example 6

Scheme 6

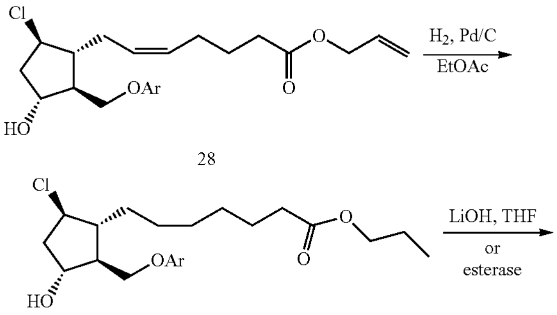

28

29

-continued

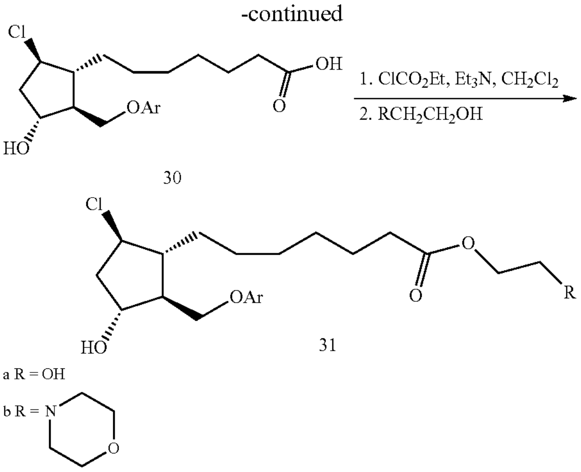

30

31

Step 1: Hydrogenation of 28 to Give 29.

Palladium on carbon (10 wt. %, 3 mg) was added to a solution of 28 (12 mg, 0.023 mmol) in EtOAc (0.5 mL). A hydrogen atmosphere was established by evacuating and refilling with hydrogen (5×) and the reaction mixture was stirred under a balloon of hydrogen for 4 h. The reaction mixture was filtered through celite, washing with EtOAc, and the filtrate was concentrated in vacuo to afford 12 mg (99%) of propyl ester 29.

Step 2: Saponification of 29 to Give 30.

Lithium hydroxide (0.1 mL of a 1.0 M aqueous solution, 0.1 mmol) was added to a solution of ester 29 (10 mg, 0.019 mmol) in THF (0.19 mL). The mixture was heated at 40° C. for 3 h, then cooled and the solvent was removed under a stream of nitrogen. $H_2O$ (2 mL) was added, the mixture was acidified with 1.0 M aqueous HCl (0.5 mL), and the resulting cloudy solution was extracted with EtOAc (3×10 mL). The combined extracts were washed with brine (10 mL), dried ($Na_2SO_4$), filtered and concentrated in vacuo. Purification of the crude residue by flash column chromatography on silica gel (25%→50% EtOAc/hexane, gradient) afforded 8.5 mg (85%) starting material 29 and 1.3 mg (14%) of compound 30.

Step 3: Conversion of 30 to 31a and 31b

Compound 30 is converted to compound 31a and 31b in accordance with the procedure in Examples 1, Step 8.

Example 7

Scheme 7

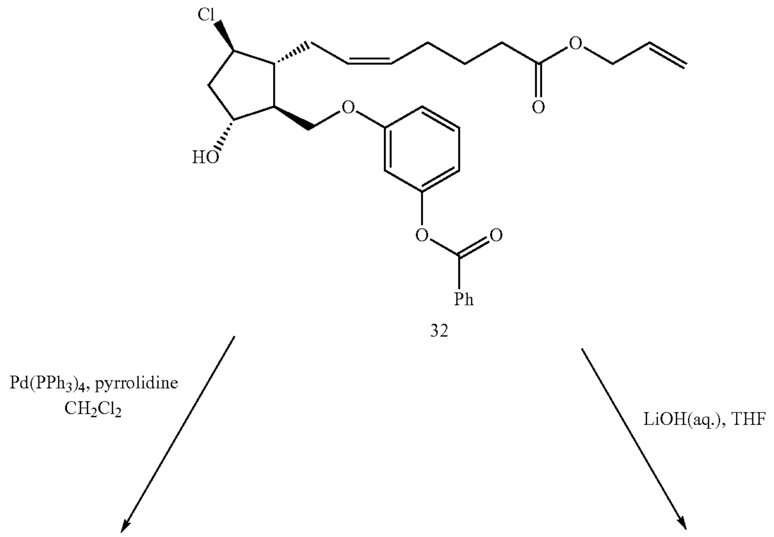

32

-continued

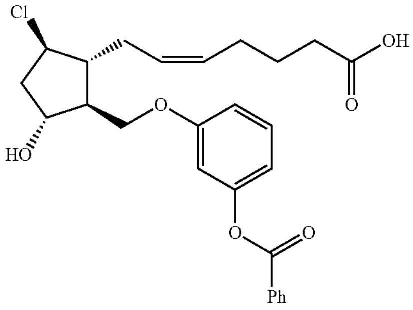

33

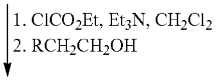

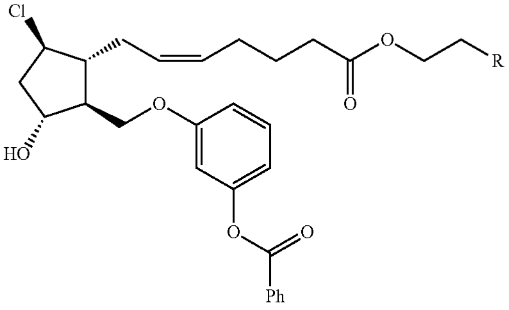

34

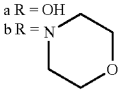

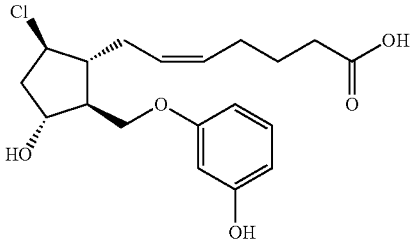

35

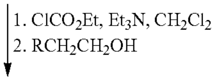

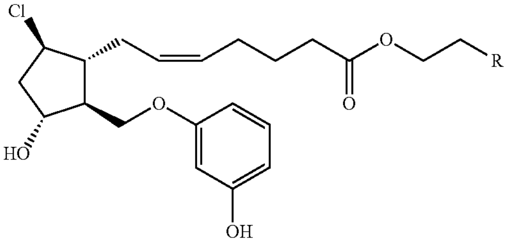

36

Step 1: Deallylation of 32 to Give 33.

Tetrakis(triphenylphosphine)palladium (2 mg, 0.0017 mmol) was added to a solution of allyl ester 32 (17.5 mg, 0.034 mmol) in $CH_2Cl_2$ (0.34 mL). The reaction mixture was cooled to 0° C. and pyrrolidine (3.1 mL, 0.037 mmol) was added. After 15 min at 0° C. the solvent was removed under a stream of nitrogen. $H_2O$ (2 mL) and 1.0 M aqueous HCl (1 mL) were added and the mixture was extracted with EtOAc (3×10 mL). The combined extracts were washed with brine (10 mL), dried ($Na_2SO_4$), filtered and concentrated in vacuo. Purification of the crude residue by flash column chromatography on silica gel (60%→80% EtOAc/hexane→EtOAc→10% MeOH/EtOAc, gradient) afforded 1.7 mg (11%) of compound 33.

Step 2: Conversion of 33 to 34a and 34b

Compound 33 is converted to compound 34a and 34b in accordance with the procedure in Examples 1, Step 8.

Compound 35

Ester 32 from was converted to compound 35 in accordance with the procedure of Example 6, step 2.

Conversion of 35 to 36a and 36b

Compound 35 is converted to compound 36a and 36b in accordance with the procedure in Examples 1, Step 8.

Example 8

Scheme 8

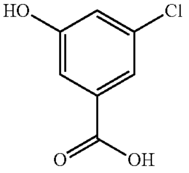

37

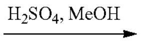

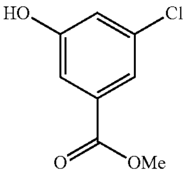

38

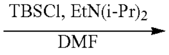

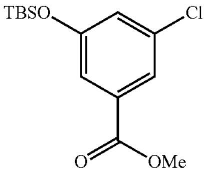

39

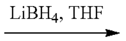

-continued

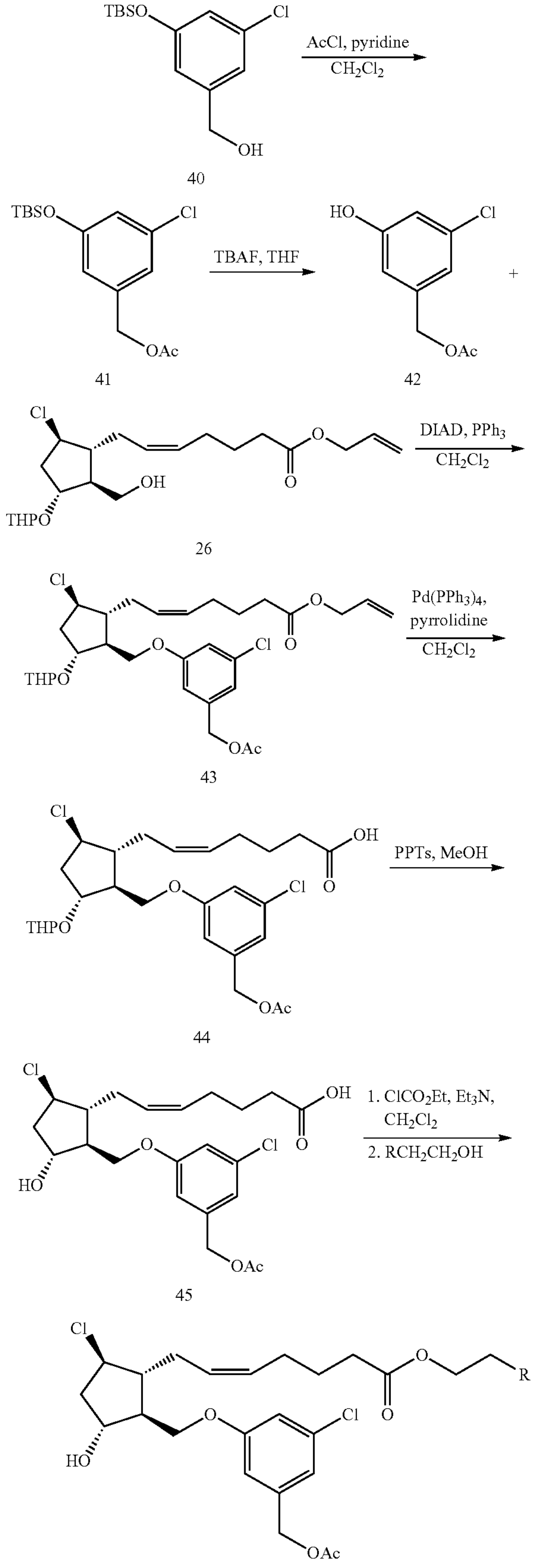

40

41

42

26

43

44

45

46

-continued a R = O b R =

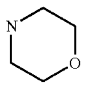

Step 1: Methylation of 37 to Give 38.

Concentrated sulfuric acid (0.04 mL, 0.48 mmol) was added to a solution of 3-chloro-5-hydroxy-benzoic acid (37, 500 mg, 2.9 mmol) in methanol (MeOH) (3.5 mL) and the resulting solution was heated at reflux for 5.5 h. The reaction was allowed to cool to room temperature then partitioned between saturated aqueous $NaHCO_3$ (50 mL) and EtOAc (50 mL). The phases were separated and the aqueous phase was extracted with EtOAc (2×20 mL). The combined organic phases were washed with brine (20 mL), dried ($MgSO_4$), filtered and concentrated in vacuo to afford 540 mg (99%) of ester 38.

Step 2: Silylation of 38 to Give 39.

Diisopropylethylamine (0.37 mL, 2.1 mmol) and tert-butyldimethylsilyl chloride (250 mg, 1.7 mmol) were added to a solution of phenol 38 (280 mg, 1.5 mmol) in DMF (1 mL) at 0° C. After 1 h, the reaction mixture was poured into EtOAc (50 mL) and $H_2O$ (25 mL). The layers were separated and the organic phase was washed with $H_2O$ (25 mL) and brine (20 mL), then dried ($MgSO_4$), filtered and concentrated in vacuo. Purification of the crude residue by flash column chromatography on silica gel (hexane→5% EtOAc/hexane) afforded 449 mg (99%) of silyl ether 39.

Step 3: Reduction of ester 39 to alcohol 40.

A solution of ester 39 (220 mg, 0.73 mmol) in THF (1 mL) was added via syringe to a suspension of $LiBH_4$ (24 mg, 1.1 mmol) in THF (0.5 mL) at 0° C. The solution was heated at reflux. The reaction was cooled to room temperature and poured into a mixture of ice and 10% acetic acid. The mixture was extracted with EtOAc. The combined organic phase was washed with $H_2O$ and brine then dried ($MgSO_4$), filtered and concentrated in vacuo. Purification of the crude residue by flash column chromatography on silica gel (10% EtOAc/hexane) afforded 149 mg (75%) of alcohol 40.

Step 4. Acylation of Alcohol 40 to Give Acetate 41.

Pyridine (49 μL, 0.61 mmol) and acetyl chloride (43 μl, 0.61 mmol) were added sequentially to a solution of alcohol 40 (150 mg, 0.55 mmol) in $CH_2Cl_2$ (1.0 mL). After 5 min, the reaction mixture was partitioned between saturated aqueous $NaHCO_3$ (10 mL) and $CH_2Cl_2$ (20 mL). The phases were separated and the aqueous phase was extracted with $CH_2Cl_2$ (2×15 mL). The combined organic phases were washed with brine (10 mL), dried ($MgSO_4$), filtered and concentrated in vacuo. Purification of the crude residue by flash column chromatography on silica gel (10% EtOAc/hexane) afforded 135 mg (78%) of acetate 41.

Step 5: Disilylation of 41 to Give Phenol 42.

Tetrabutylammonium fluoride (1.0 M in THF, 1.28 mL, 1.28 mmol) was added to a solution of silyl ether 42 (135 mg, 0.43 mmol) in THF (1.0 mL) and the reaction was allowed to stir overnight at room temperature. The reaction was then partitioned between $H_2O$ (10 mL) and EtOAc (20 mL). The layers were separated and the organic phase was washed with $H_2O$ (2×15 mL) and brine (10 mL), then dried ($MgSO_4$), filtered and concentrated in vacuo. Purification of the crude residue by flash column chromatography on silica gel (20% EtOAc/hexane) afforded 40 mg (56%) of compound 42.

Step 6:

Alcohol 26 (80 mg, 0.20 mmol) and phenol 42 (40 mg, 0.24 mmol) were converted into 70 mg (60%) of ether 43 in accordance with the procedure of Example 5, step 4.

Step 7:

Ester 43 (70 mg, 0.12 mmol) was converted into 60 mg (impure, contaminated with $PPh_3$) of acid 44 in accordance with the procedure of Example 7, step 1.

Step 8:

Ether 44 (30 mg, 0.55 mmol) was converted into 5 mg (20%) of compound 45 in accordance with the procedure of Example 5, step 5.

Step 9:

Conversion of 45 to 46a and 46b

Compound 45 is converted to compound 46a and 46b in accordance with the procedure in Examples 1, Step 8.

From the methods disclosed herein, a person of ordinary skill in the art can prepare the compounds disclosed herein by using the disclosed methods, by adaptations readily ascertainable by those in the art from the disclosure herein, and/or by the knowledge generally available in the art. Although some of these examples are specific, they should not be construed to limit the scope of the invention, but rather as being presented for the purpose of guiding those skilled in the art in making the compounds disclosed herein.

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states “a wedge indicates a bond coming from the plane of the paper toward the viewer” and the hatched wedge, indicated as a “dashed line”, “represents a bond receding from the viewer.” Unless stereochemistry is explicitly depicted, a structure is intended to include every possible stereoisomer, both pure or in any possible mixture. Unless stereochemistry is explicitly depicted, a structure is intended to include every possible stereoisomer, both pure or in any possible mixture.

IN VIVO EXAMPLES

An aqueous liquid containing 0.1% of compound 10a is given topically to the eye of a person suffering from elevated intraocular pressure. A few hours after administration, the person’s intraocular pressure is reduced.

An aqueous liquid containing 0.1% of compound 10b is given topically to the eye of a person suffering from elevated intraocular pressure. A few hours after administration, the person’s intraocular pressure is reduced.

An aqueous liquid containing 0.1% of compound 11a is given topically to the eye of a person suffering from elevated intraocular pressure. A few hours after administration, the person’s intraocular pressure is reduced.

An aqueous liquid containing 0.1% of compound 11b is given topically to the eye of a person suffering from elevated intraocular pressure. A few hours after administration, the person’s intraocular pressure is reduced.

An aqueous liquid containing 0.1% of compound 14a is given topically to the eye of a person suffering from elevated intraocular pressure. A few hours after administration, the person’s intraocular pressure is reduced.

An aqueous liquid containing 0.1% of compound 14b is given topically to the eye of a person suffering from elevated intraocular pressure. A few hours after administration, the person’s intraocular pressure is reduced.

An aqueous liquid containing 0.1% of compound 19a is given topically to the eye of a person suffering from elevated intraocular pressure. A few hours after administration, the person’s intraocular pressure is reduced.

An aqueous liquid containing 0.1% of compound 19b is given topically to the eye of a person suffering from elevated intraocular pressure. A few hours after administration, the person’s intraocular pressure is reduced.

An aqueous liquid containing 0.1% of compound 22a is given topically to the eye of a person suffering from elevated intraocular pressure. A few hours after administration, the person’s intraocular pressure is reduced.

An aqueous liquid containing 0.1% of compound 22b is given topically to the eye of a person suffering from elevated intraocular pressure. A few hours after administration, the person’s intraocular pressure is reduced.

An aqueous liquid containing 0.1% of compound 30a is given topically to the eye of a person suffering from elevated intraocular pressure. A few hours after administration, the person’s intraocular pressure is reduced.

An aqueous liquid containing 0.1% of compound 30b is given topically to the eye of a person suffering from elevated intraocular pressure. A few hours after administration, the person’s intraocular pressure is reduced.

An aqueous liquid containing 0.1% of compound 31a is given topically to the eye of a person suffering from elevated intraocular pressure. A few hours after administration, the person’s intraocular pressure is reduced.

An aqueous liquid containing 0.1% of compound 31b is given topically to the eye of a person suffering from elevated intraocular pressure. A few hours after administration, the person’s intraocular pressure is reduced.

An aqueous liquid containing 0.1% of compound 34a is given topically to the eye of a person suffering from elevated intraocular pressure. A few hours after administration, the person’s intraocular pressure is reduced.

An aqueous liquid containing 0.1% of compound 34b is given topically to the eye of a person suffering from elevated intraocular pressure. A few hours after administration, the person’s intraocular pressure is reduced.

An aqueous liquid containing 0.1% of compound 36a is given topically to the eye of a person suffering from elevated intraocular pressure. A few hours after administration, the person’s intraocular pressure is reduced.

An aqueous liquid containing 0.1% of compound 36b is given topically to the eye of a person suffering from elevated intraocular pressure. A few hours after administration, the person’s intraocular pressure is reduced.

An aqueous liquid containing 0.1% of compound 46a is given topically to the eye of a person suffering from elevated intraocular pressure. A few hours after administration, the person’s intraocular pressure is reduced.

An aqueous liquid containing 0.1% of compound 46b is given topically to the eye of a person suffering from elevated intraocular pressure. A few hours after administration, the person’s intraocular pressure is reduced.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.
What is claimed is:
1. A compound having a formula selected from:
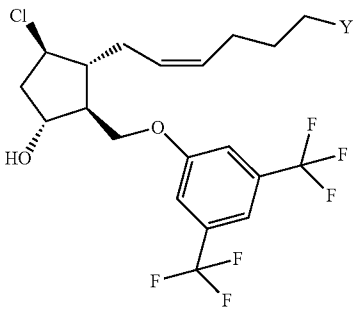
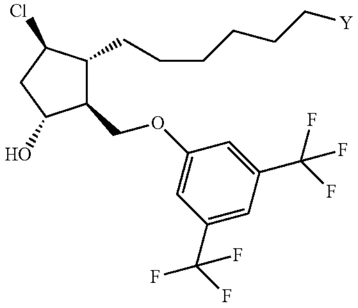
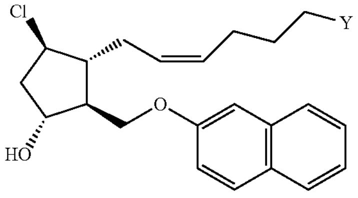
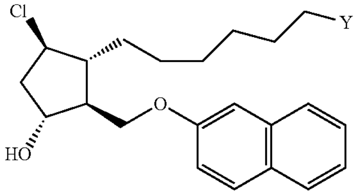
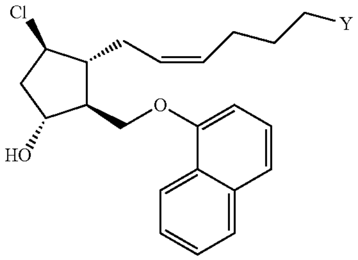
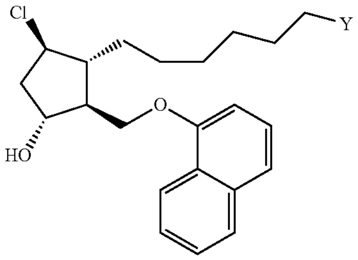
-continued
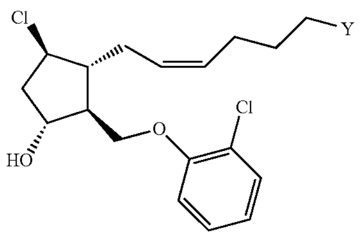
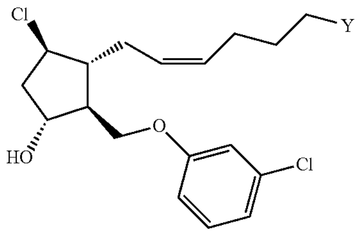
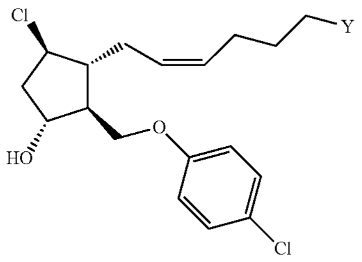
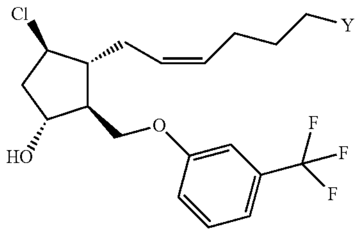
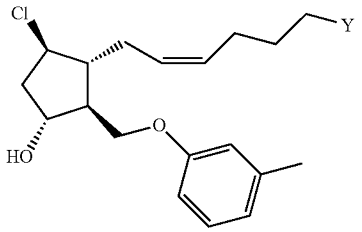
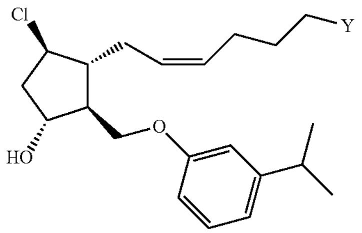
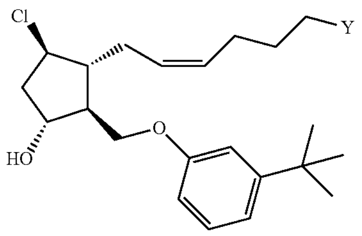

-continued
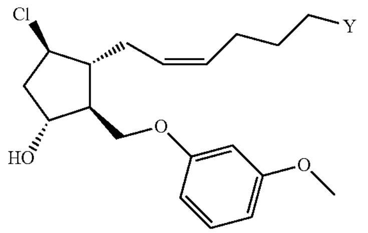
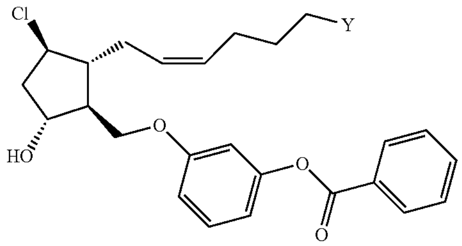
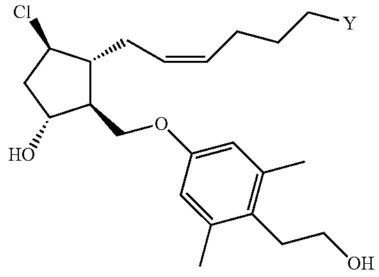
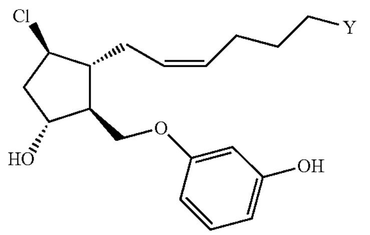
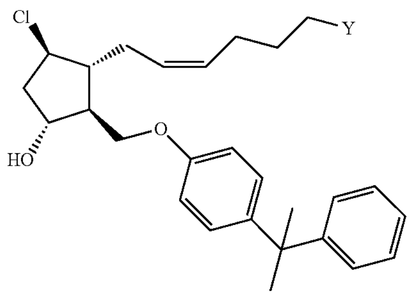
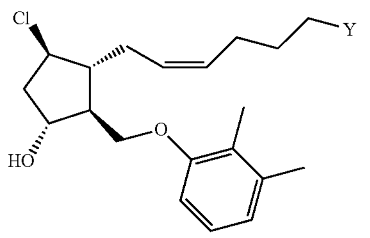
-continued
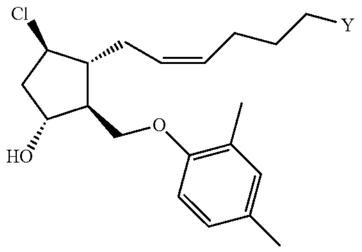
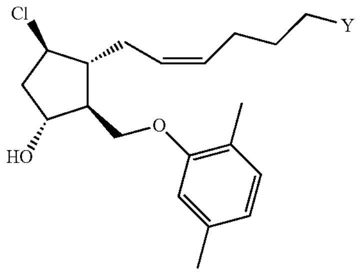
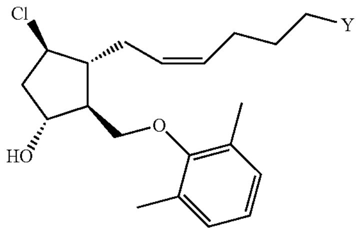
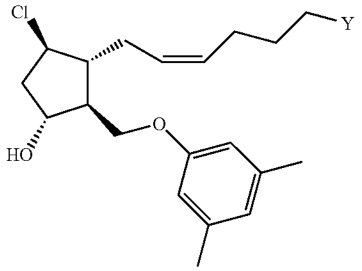
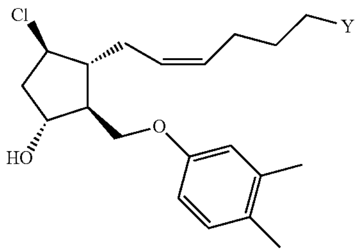
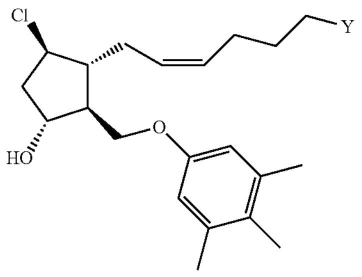

-continued
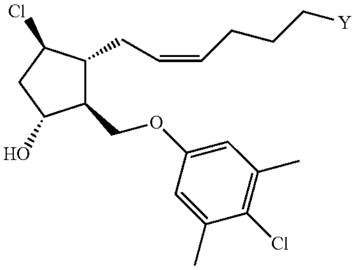
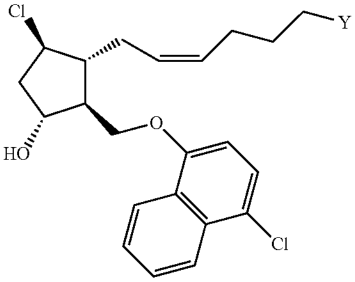
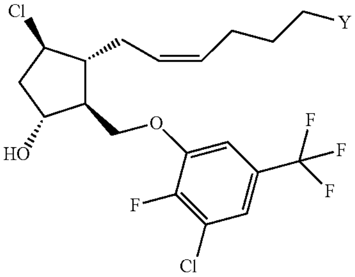
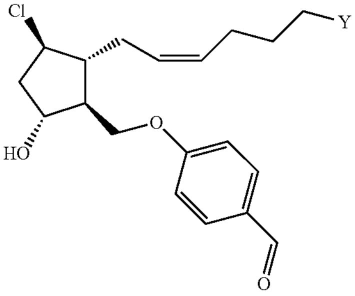
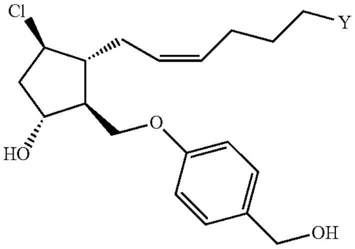
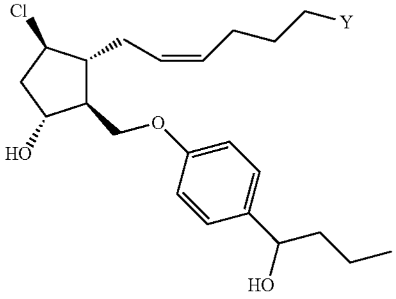
-continued
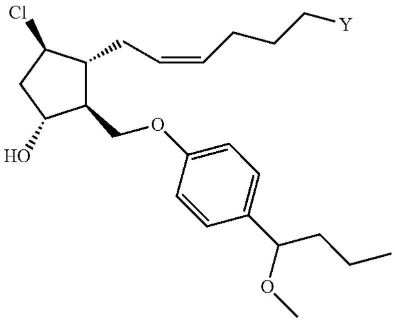
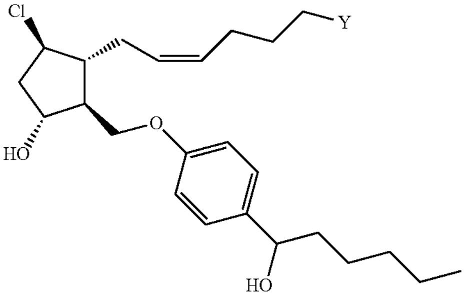
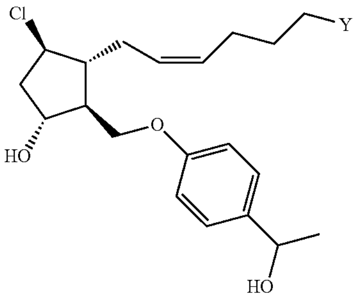
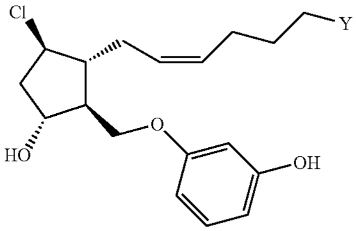
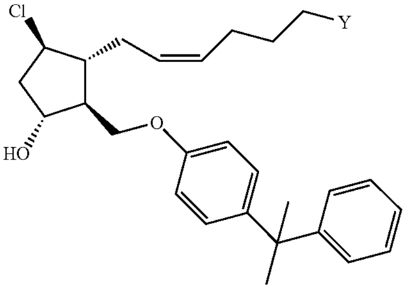
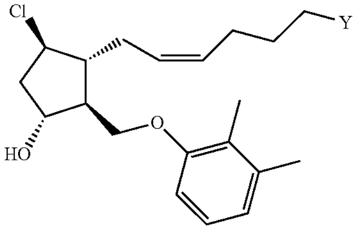

-continued
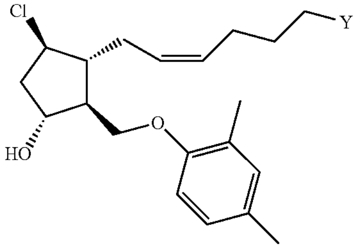
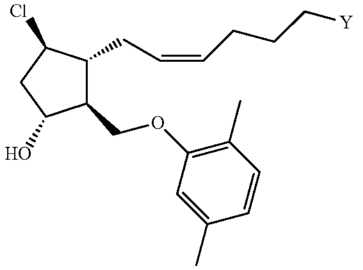
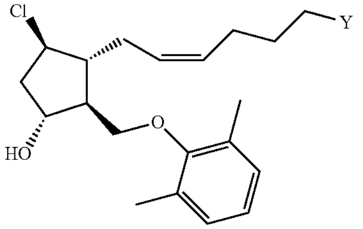
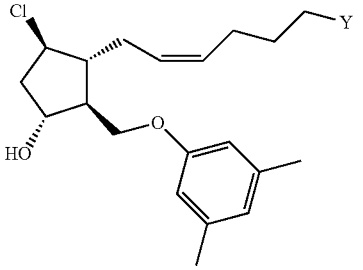
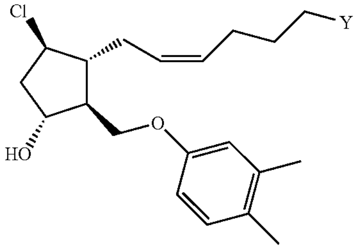
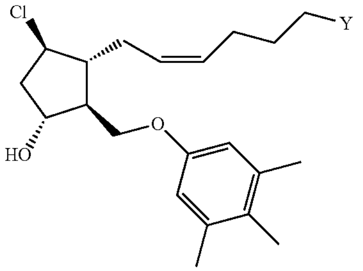
-continued
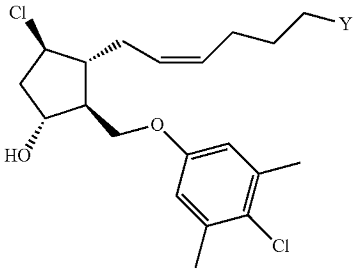
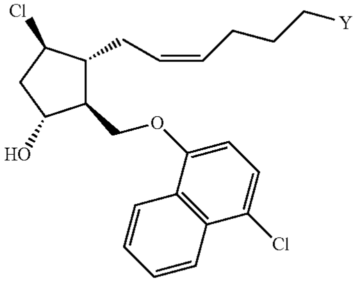
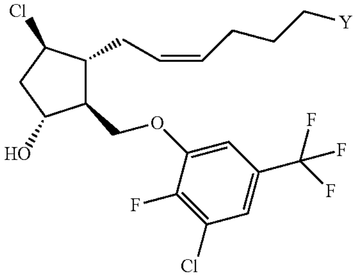
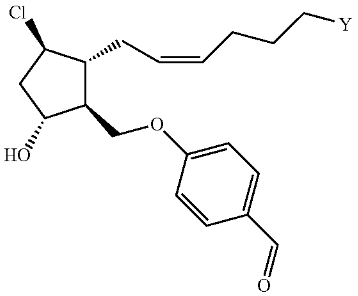
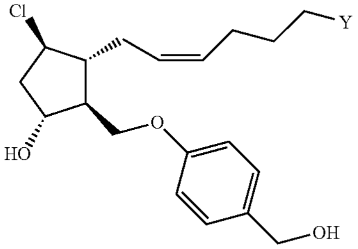
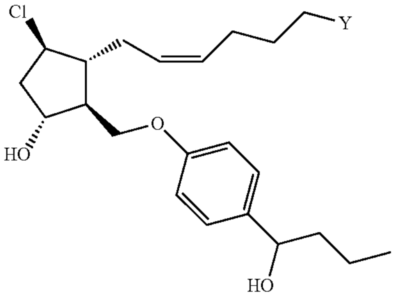

-continued

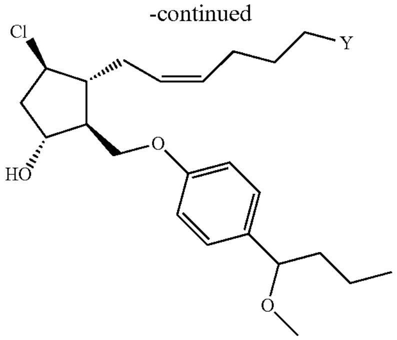

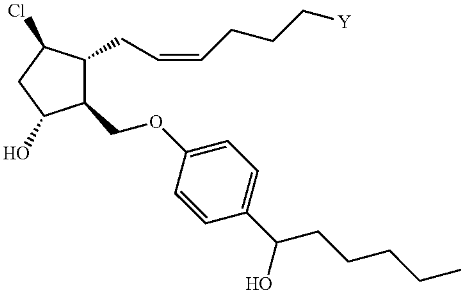

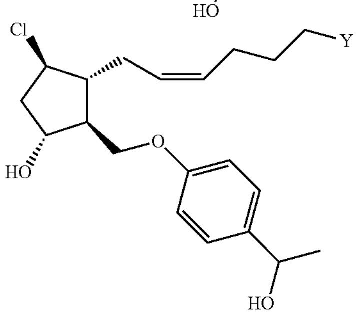

wherein Y is

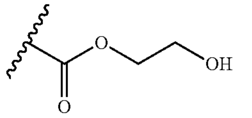

or

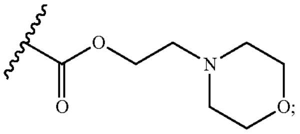

or a pharmaceutically acceptable salt thereof.

2. The compound of claim 1 according to the formula

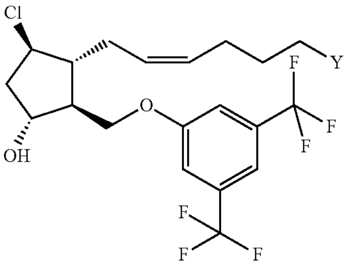

or a pharmaceutically acceptable salt thereof.

3. The compound of claim 1 according to the formula

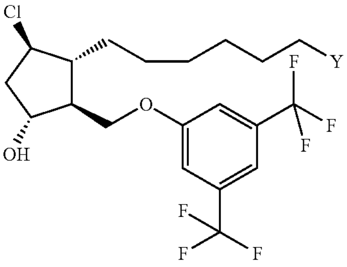

or a pharmaceutically acceptable salt thereof.

4. The compound of claim 1 according to the formula

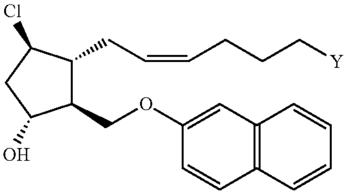

or a pharmaceutically acceptable salt thereof.

5. The compound of claim 1 according to the formula

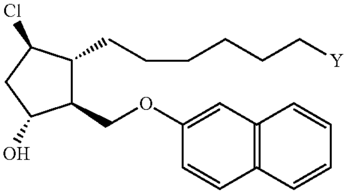

or a pharmaceutically acceptable salt thereof.

6. The compound of claim 1 according to the formula

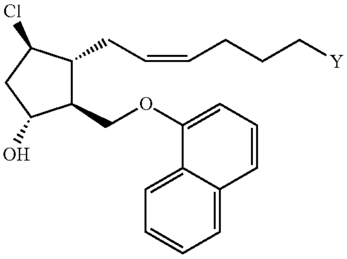

or a pharmaceutically acceptable salt thereof.

7. The compound of claim 1 according to the formula

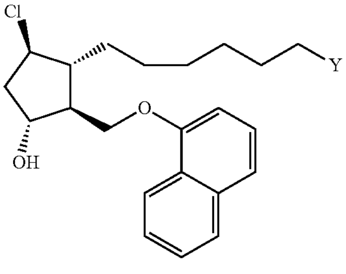

or a pharmaceutically acceptable salt thereof.

8. The compound of claim 1 according to the formula

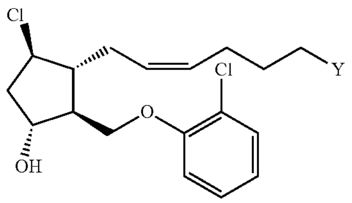

or a pharmaceutically acceptable salt thereof.

9. The compound of claim 1 according to the formula

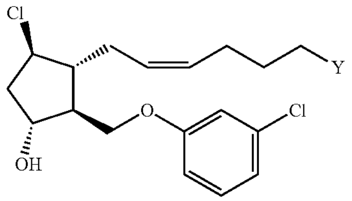

or a pharmaceutically acceptable salt thereof.

10. The compound of claim 1 according to the formula

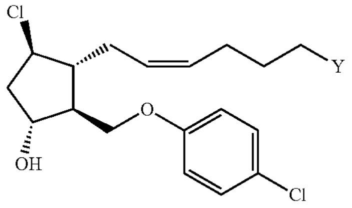

or a pharmaceutically acceptable salt thereof.

11. The compound of claim 1 according to the formula

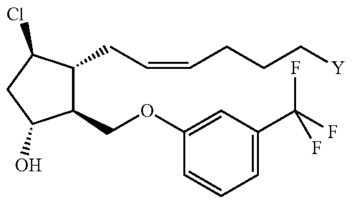

or a pharmaceutically acceptable salt thereof.

12. The compound of claim 1 according to the formula

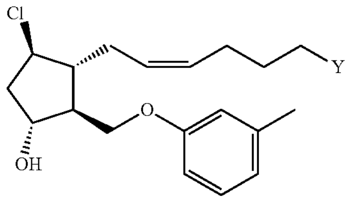

or a pharmaceutically acceptable salt thereof.

13. The compound of claim 1 according to the formula

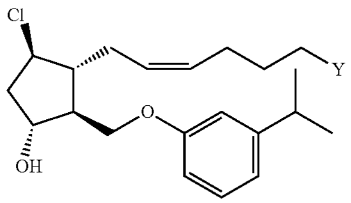

or a pharmaceutically acceptable salt thereof.

14. The compound of claim 1 according to the formula

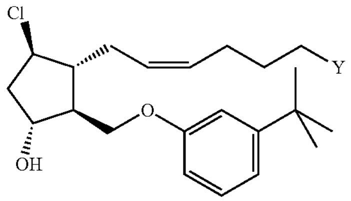

or a pharmaceutically acceptable salt thereof.

15. The compound of claim 1 according to the formula

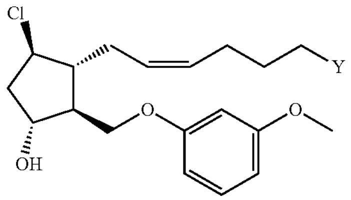

or a pharmaceutically acceptable salt thereof.

16. The compound of claim 1 according to the formula

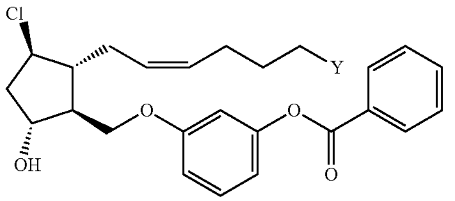

or a pharmaceutically acceptable salt thereof.

17. The compound of claim 1 according to the formula

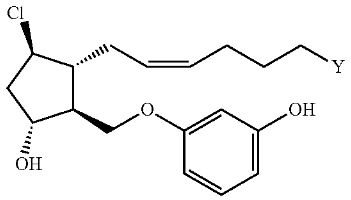

or a pharmaceutically acceptable salt thereof.

18. The compound of claim 1 according to the formula

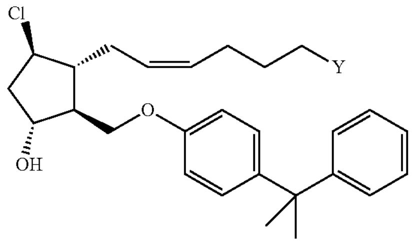

or a pharmaceutically acceptable salt thereof.

19. The compound of claim 1 according to the formula

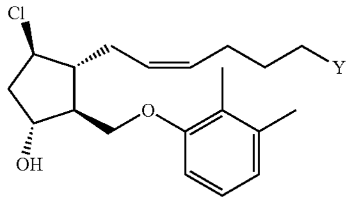

or a pharmaceutically acceptable salt thereof.

20. The compound of claim 1 according to the formula

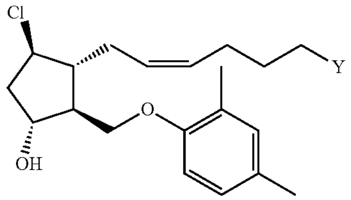

or a pharmaceutically acceptable salt thereof.

21. A method of treating baldness comprising administering to a subject in need thereof a therapeutically effective amount of a compound of claim 1.

* * * * *